United States Patent [19]

Sugihara et al.

[11] Patent Number: 4,880,809
[45] Date of Patent: Nov. 14, 1989

[54] 1,4-DISUBSTITUTED PIPERAZINES (OR HOMOPIPERAZINES) AS PLATELET-ACTIVATING FACTOR ANTAGONISTS

[75] Inventors: Hirosada Sugihara; Katsumi Itoh, both of Osaka; Kohei Nishikawa, Kyoto, all of Japan

[73] Assignee: Takeda Chemical Industries, Ltd., Osaka, Japan

[21] Appl. No.: 167,961

[22] Filed: Mar. 14, 1988

[30] Foreign Application Priority Data

Mar. 24, 1987 [JP] Japan ................... 62-69804

[51] Int. Cl.$^4$ ............ A61K 31/495; A61K 31/55; C07D 295/10; C07D 243/08
[52] U.S. Cl. ................... 514/255; 514/218; 540/575; 544/386; 544/387
[58] Field of Search ............ 544/386, 387; 514/255, 514/218; 540/575

[56] References Cited

U.S. PATENT DOCUMENTS

| | | | |
|---|---|---|---|
| 4,130,646 | 12/1978 | Vogt et al. | 544/394 |
| 4,148,897 | 4/1979 | Oka et al. | 544/173 |
| 4,252,804 | 2/1981 | Joullié et al. | 544/394 |
| 4,308,266 | 12/1981 | Seiler | 544/394 |
| 4,370,330 | 1/1983 | Scherm et al. | 544/394 |

FOREIGN PATENT DOCUMENTS

| | | |
|---|---|---|
| 0171636 | 2/1986 | European Pat. Off. |
| 190685 | 8/1986 | European Pat. Off. ............ 544/387 |
| 55879 | 3/1984 | Japan ................... 544/387 |

OTHER PUBLICATIONS

Purcell, William P., et al., "Application of Regression Analyses to Antitumor Activities of Various Acetylenic Carbamates", Journal of Medicinal Chemistry, vol. 11, No. 2, pp. 390-391, Feb. 26, 1968.
Chemical Abstracts, vol. 59, 6404a (1963).
Chemical Abstracts, vol. 79, 42553u (1973).
Chemical Abstracts, vol. 88, 136677a (1978).
Chemical Patents Index Basic Abstracts Journal Section B, 86-179263/28, Japanese Unexamined Patent Publication No. 112060/1986.
Chemical Patents Index Basic Abstracts Journal Section B, 87-016682/03, Japanese Unexamined Patent Publication No. 233675/1986.
Chemical & Pharmaceutical Bulletin, vol. 31, pp. 2006-2015 (1983).
Life Sciences, vol. 32, pp. 1975-1982 (1983).
Cerbai et al, CA 6403-6404, "Neurosedative and Hypotensive Effects in Acylic Derivatives of Heterocyclic Bases."

Primary Examiner—Cecilia Shen
Attorney, Agent, or Firm—Wegner & Bretschneider

[57] ABSTRACT

Novel 1,4-disubstituted piperazine compounds represented by the formula (I):

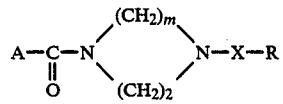

wherein
A is a condensed polycyclic hydrocarbon group;
R is a phenyl group substituted with a lower alkoxy group;
X is methylene group, carbonyl group or thiocarbonyl group;
and m is 2 or 3, and their salts
are useful as a platelet activating factor antagonist.

25 Claims, No Drawings

1,4-DISUBSTITUTED PIPERAZINES (OR HOMOPIPERAZINES) AS PLATELET-ACTIVATING FACTOR ANTAGONISTS

BACKGROUND OF THE INVENTION

This invention relates to 1,4-disubstituted piperazine compounds useful as medicines, their production and use. More specifically, the present invention relates to compounds represented by the formula:

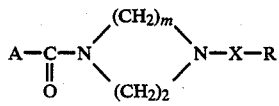

(I)

wherein A stands for a condensed polycyclic hydrocarbon group, R stands for a phenyl group substituted with a lower alkoxy group, X stands for a methylene group, alkcarbonyl group or thiocarbonyl group, and m denotes 2 or 3 and their salts, which are useful as platelet activating factor (PAF) antagonists.

PAF has a phospholipid structure and is a chemical transmitter existing in a living body. It has been made clear that PAF is, in a living body, closely concerned with allergy, anaphylaxis, inflammation, etx. and it has also been known that PAF has a strong hypotensive activity and platelet agglutinating activity. On administering PAF to an animal, the animal may in some cases be killed from shock. Symptoms caused by the shock from PAF have much resemblance to those caused by the shock from endotoxin, and it has been considered that PAF is concerned with the endotoxin shock.

On the other hand, while a variety of compounds having PAF-antagonistic activity have been known, very few of them are satisfactory in PAF-antagonistic activity in a living body. And, even when then PAF-antagonistic activity in a living body is satisfactory, not a few of those compounds have some restrictions in the administration method.

DETAILED DESCRIPTION

The object of the present invention is to provide novel 1,4-disubstituted piperazine compounds represented by the formula (I) and their salts, which are excellent in absorption from the intestinal canal and show excellent PAF antagonism even by oral administration.

Referring to the formula (I), examples of the condensed polycyclic hydrocarbon groups shown by A include bicyclic or tricylic hydrocarbon groups which may optionally be saturated partially, more specifically, hydrocarbon groups formed by condensation of two or three 5- to 8-membered rings, such as pentalenyl, indenyl (1H-indenyl, 2H-indenyl), indanyl, naphthyl, dihydronaphthyl (1,2-dihydronaphthyl, 2,3-dihydronaphthyl), tetrahydronaphthyl (1,2,3,4-tetrahydronaphthyl etc.), hexahydronaphthyl (1,2,3,4,5,6-hexahydronaphthyl etc.), azulenyl, heptalenyl, biphenylenyl, indacenyl (as-indacenyl, s-indacenyl), acenaphthlenyl, acenaphthenyl, phenalenyl, phenanthryl, dihydrophenanthryl (1,2-dihydrophenanthryl), tetrahydrophenanthryl (1,2,3,4-tetrahydrophenanthryl, etc.), hexahydrophenanthryl, anthryl, dihydroanthryl, (9,10-dihydroanthryl, etc.), tetrahydroanthryl, hexahydroanthryl, octahydroanthryl, fluorenyl (3H-fluorenyl, 9H-fluorenyl, etc.), dihydrofluorenyl, tetrahydrofluorenyl, benzocycloheptenyl (5H-benzocycloheptenyl, etc.), dihydrobenzocycloheptenyl (6,7-dihydro-5H-benzocycloheptenyl, etc.), tetrahydrobenzocycloheptenyl (6,7,8,9-tetrahydro-5H-benzocycloheptenyl, etc.), dibenzocycloheptenyl (5H-dibenzo[a,b]cycloheptenyl, 5H-dibenzo[a,c]cycloheptenyl, etc.), naphthocycloheptenyl (6H-naphtho[b]cycloheptenyl, etc.), dihydronaphthocycloheptenyl (7,8-dihydro-6H-naphtho[b]cycloheptenyl, etc.), benzocyclooctenyl, dihydrobenzocyclooctenyl (5,6-dihydrobenzocyclooctenyl, etc.), tetrahydrobenzocyclooctenyl (5,6,7,8-tetrahydrobenzocyclooctenyl, etc.), hexahydrobenzocyclooctenyl, octahydrobenzocyclooctenyl, etc.

These condensed polycyclic hydrocarbon groups shown by the above A include those having one or more (preferably not more than 4) substituents such as, among other, a lower alkyl group, a halo lower alkyl group, a hydroxy lower alkyl group, an acyloxy lower alkyl group, a lower alkoxy-lower alkyl group, a lower alkoxy group, a halo lower alkoxy group, a lower alkoxy carbonyl-lower alkoxy group, a lower alkenyloxy group, aralkyloxy group, a lower alkoxy-lower alkoxy group, a lower alkoxycarbonyl group, carboxyl group, carbamoyl group, a N,N-di-lower alkylcarbamoyl group, an N-lower alkyl carbamoyl group, halo group, cyano group, nitro group, hydroxy group, acyloxy group, amino group, a lower alkylsufonylamino group, acylamino group, a lower alkoxycarbonylamino group, acyl group, mercapto group, a lower alkylthio group, a lower alkylsufinyl group, a lower alkylsufonyl group and oxo group. When the condensed polycyclic hydrocarbon group has two or more substituents, the kinds of these substituents may be the same or different from one another.

Lower alkyl groups as the above-mentioned substituents are exemplified by alkyl groups whose carbon number ranges from about 1 to about 4, such as methyl, ethyl, propyl, isopropyl, butyl, isobutyl, sec-butyl, tert-butyl, etc. As the halo lower alkyl group, mention is made of alkyl groups whose carbon number ranges from about 1 to about 4, which are substituted with 1 to 3 halo groups such as trifluoromethyl, fluoromethyl, chloromethyl, chloroethyl, fluoroethyl, etc. As the hydroxy lower alkyl group, mention is made of hydroxy alkyl groups whose carbon number ranges from about 1 to about 4, such as hydroxymethyl, hydroxyethyl, hydroxypropyl, hydroxybutyl, etc. As the acyloxy lower alkyl group, mention is made of alkyl groups whose carbon number ranges from about 1 to 4, which are substituted with, for example, a lower alkanoyloxy group whose carbon number ranges from about 2 to about 5 such as acetoxyethyl, etc. or a benzoyloxy group such as benzoyloxyethyl, etc. As the lower alkoxy-lower alkyl group, mention is made of alkyl groups whose carbon number ranges from about 1 to about 4, which are substituted with, for example, an alkoxy group whose carbon number ranges from about 1 to about 4 such as methoxyethyl, ethoxyethyl, propoxyethyl, butoxyethyl, methoxypropyl, methoxybutyl, ethoxypropyl, ethoxybutyl etc. As the lower alkoxy group, mention is made of alkoxy groups whose carbon number ranges from about 1 to about 4 such as methoxy, ethoxy, propoxy, isopropoxy, butoxy, isobutoxy, sec-butoxy, tert-butoxy, etc. As the halo lower alkoxy group, mention is made of alkoxy groups whose carbon number ranges from about 1 to about 4, which are substituted with 1 to 3 halo groups such as chloroethoxy, fluoroethoxy, difluoroethoxy, trifluoroethoxy, chloropropoxy, chlorobutoxy, etc. As the lower alkoxy carbonyl-lower alkoxy group, mention is made of alkoxy groups whose carbon number ranges from about 1 to about 4, which are substituted with an alkoxycarbonyl group, the carbon number of the alkoxy moiety of which ranges from about 1 to about 4, such as methoxycarbonylmethoxy, ethoxycarbonylmethoxy, butoxycarbonylmethoxy, methoxycarbonylpropoxy, ethoxycarbonylethoxy, etc. Examples of the lower alkenyloxy group include alkenyloxy groups whose carbon number ranges from about 2 to about 5, such as vinyloxy, allyloxy, butenyloxy, etc. As the aralkyloxy group, mention is made of phenyl lower alkyloxy groups, the carbon number of the lower alkyl moiety of which ranges from about 1 to about 4, such as benzyloxy, phenethyloxy, 3-phenylpropyloxy, α-methylphenethyloxy, α-methylbenzyloxy, α-ethylbenzyloxy, βethylphenethyloxy, β-methylphenthyloxy, etc. As the lower alkoxy-lower alkoxy group, mention is made of alkoxy groups whose carbon number ranges from about 1 to about 4, which are substituted with, for example, an alkoxy group whose carbon number ranges from about 1 to about 4, such as ethoxymethoxy, methoxyethoxy, butoxyethoxy, ethoxypropoxy, etc. Examples of the lower alkoxycarbonyl group include alkoxycarbonyl groups, the carbon number of the alkoxy moiety of which ranges from about 1 to about 4, such as methoxycarbonyl, ethoxycarbonyl, propoxycarbonyl, butoxycarbonyl, etc. As the N,N-di-lower alkylcarbamoyl group, mention is made of N,N-dialkylcarbamoyl groups, the carbon number of each alkyl moiety of which ranges from about 1 to about 4, such as N,N-dimethylcarbamoyl, N,N-diethylcarbamoyl, N,N-dipropylcarbamoyl, N,N-dibutylcarbamoyl, N-ethyl-N-memethylcarbamoy, etc., and groups forming 5- or 6-membered ring structure (e.g. pyrrolidinylcarbonyl, piperidinocarbonyl) by combining dialkyl moieties together. As the N-lower alkylarbamoyl gorup, mention is made of N-alkylcarbamoyl groups, the carbon number of the alkyl moiety of which ranges from about 1 to about 4, such as N-methylcarbamoyl, N-ethylcarbamoyl, N-propylcarbamoyl, N-butylcarbamoyl, etc. As the halo group, mention is made of halogeno groups such as chloro, fluoro, bromo, iodo, etc. As the acyloxy group, mention is made of alkanoyloxy groups, the carbon number of which ranges from about 2 to about 5, such as acetoxy, propanoyloxy, butyryloxy, pivaloyloxy, etc., and benzoyloxy group. As the lower alkylsulfonylamino group, mention is made of alkylsulfonylamino groups, the carbon number of which ranges from about 1 to about 4, such as methanesulfonylamino, ethanesulfonylamino, etc. Examples of the acylamino group include alkanoylamino groups, whose carbon number ranges from about 2 to about 5, such as acetylamino, propanoylamino, butyrylamino, pivaloylamino, etc. and benzoylamino. As the alkoxycarbonylamino group, mention is made of alkoxycarbonylamino groups, the carbon number of the alkoxy moeity of which ranges from about 1 to about 4, such as methoxycarbonylamino, ethoxycarbonylamino, propoxycarbonylamino, butoxycarbonylamino, etc. As the acyl group, mention is made of alkanoyl groups, the carbon number of which ranges from about 2 to about 5, such as acetyl, propanoyl, butyryl, pivaloyl, etc., and bezoyl group. As the lower alkylthio group, mention is made of alkylthio groups, the carbon number of which ranges from about 1 to about 4, such as methylthio, ethylthio, propylthio, butylthio, etc. As the lower alkylsufinyl group, mention is made of alkylsufinyl groups, the carbon number of which ranges from about 1 to about 4, such as methylsufinyl, ethylsulfinyl, propylsulfinyl, butylsulfinyl, etc. As the lower alkylsulfonyl group, mention is made of alkylsufonyl groups, the carbon number of which ranges from about 1 to about 4, such as methylsulfonyl, ethylsulfonyl, propylsulfonyl, butylsulfonyl, etc.

Specific examples of the condensed polycyclic hydrocarbon group shown by the above-mentioned A include 1-naphthyl, 2-naphthyl, 1-methoxy-2-naphthyl, 3-methoxy-2-naphthyl, 6-methoxy-2-naphthyl, 6,7-dimethoxy-2-naphthyl, 5,6,7-trimethoxy-2-naphthyl, 6-butoxy-2-naphthyl, 6,7-dibutoxy-2-naphthyl, 7-methoxy-1,2-dihydro-3-naphthyl, 6,7-dimethoxy-1,2-dihydro-3-naphthyl, 7,8-dimethoxy-1,2-dihydro-4-naphthyl, 6,7,8-trimethoxy-1,2-dihydro-3-naphthyl, 6,7-diethoxy-1,2-dihydro-3-naphthyl, 6,7-dipropoxy-1,2-dihydro-3-naphthyl, 6,7-dibutoxy-1,2-dihydro-3-naphthyl, 7-benzyloxy-1,2-dihydro-3-naphthyl, 7-hydroxy-1,2-dihydro-3-naphthyl, 6,7-dibenzyloxy-1,2-dihydro-3-naphthyl, 6,7-dihydroxy-1,2-dihydro-3-naphthyl, 6-methoxy-1,2,3,4-tetrahydro-2-naphthyl, 7-acetoxy-1,2-dihydro-3-naphthyl, 6,7-diacetoxy-1,2-dihydro-3-naphthyl, 7-benzoyloxy-1,2-dihydro-3-naphthyl, 6,7-dibenzoyloxy-1,2-dihydro-3-napthyl, 7-methoxy-8-nitro-1,2-dihydro-3-naphthyl, 7-methoxy-6-methoxy-6-nitro-1,2-dihydro-3-naphthyl, 6,7-dimethoxy-8-nitro-1,2-dihydro-3-naphthyl, 7-ethoxycarbonylmethoxy-1,2-dihydro-3-naphthyl, 7-(2-methoxyethoxy)-1,2-dihydro-3-naphthyl, 6,8-dimethyl-1,2-dihydro-3-naphthyl, 6-hydroxymethyl-7-methoxy-1,2-dihydro-3-naphthyl, 6,8-dimethyl-7-nitro-1,2-dihydro-3-naphthyl, 7-(2-hydroxyethoxy)-1,2-dihydro-3-naphthyl, 7-(2,3-dimethoxypropoxy)-1,2-dihydro-3-naphthyl, 7-(3-methoxypropoxy)-1,2-dihydro-3-naphthyl, 6,7-bis (2-methoxyethoxy)-1,2-dihydro-3-naphthyl, 5,6-dimethoxy-2-indanyl, 5,6-dimethoxy-1H-2-indenyl, 3,4-dimethoxy-6,7-dihydro-5H-8-benzocycloheptenyl, 2,3-dimethoxy-6,7-dihydro-5H-8-benzocycloheptenyl, 2,3-diethoxy-6,7-dihydro-5H-8-benzocycloheptenyl, 2,3-dipropoxy-6,7-dihydro-5H-8-benzocycloheptenyl, 2,3-dibutoxy-6,7-dihydro-5H-8-benzocycloheptenyl, 2-benzyloxy-3-methoxy-6,7-dihydro-5H-8-benzocycloheptenyl, 2-ethoxy-3-methoxy-6,7-dihydro-5H-8-benzocycloheptenyl, 2-propoxy-3-methoxy-6,7-dihydro-5H-8-benzocycloheptenyl, 2-butoxy-3-methoxy-6,7-dihydro-5H-8-benzocycloheptenyl, 3-methoxy-6,7-dihydro-5H-8-benzocycloheptenyl, 3-ethoxy-6,7-dihydro-5H-8-benzocycloheptenyl, 3-propoxy-6,7-dihydro-5H-8-benzocycloheptenyl, 3-butoxy-6,7-dihydro-5H-8-benzocycloheptenyl, 2,3-dimethyl-6,7-dihydro-5H-8-benzocycloheptenyl, 3-benzyloxy-6,7-dihydro-5H-8-benzocycloheptenyl, 6,7-dihydro-5H-8-benzocycloheptenyl, 1,2,3-trimethoxy-6,7-dihydro-5H-8-benzocycloheptenyl, 7-ethoxy-1,2-dihydro-3-naphthyl, 7-propoxy-1,2-dihydro-3-naphthyl, 7-butoxy-1,2-dihydro-3-naphthyl, 2,3-dimethoxy-5,6,7,8-tetrahydro-9-benzocyclooctenyl, 5,6,7,8-tetrahydro-9-benzocyclooctencyl, 2,3-dihydro-3-naphthyl, 1-indanyl, 2-indanyl, 1H-2-indenyl, 2,3-dimethoxy-6,7,8,9-tetrahydro-5H-6-benzocycloheptenyl, 6,7-dimethoxy-1-hydroxy-2-naphthyl, 6-mercapto-2-naphthyl, 6-methylthio-2-naphthyl, 6-methanesulfonyl-2-naphthyl, 1-oxo-1,2,3,4-tetrahydro-6-naphthyl, 1-oxo-1,2,3,4-tetrahydro-7-naphthyl, 1-oxo-5-indanyl, 1-oxo-6-indanyl, 1-hydroxy-1,2,3,4-tetrahydro-6-naphthyl, 1-hydroxy-1,2,3,4-tetrahydro-7-naphthyl, 1- hydroxy-5-indanyl, 1-hydroxy-6-indanyl, 9-oxo-2-fluorenyl, 9-hydroxy-2-fluorenyl, 2-anthraquinonyl, etc.

As A, condensed polycyclic hydrocarbon groups represented by the formula:

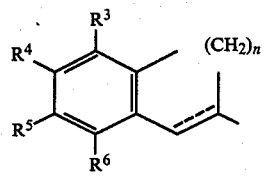

wherein the dotted line designates the presence or absence of a double bond (more preferably the presence of double bond), n denotes an integer of 1 to 4 (more preferably 2 or 3), and $R^3$, $R^4$, $R^5$ and $R^6$ independently stand for hydrogen, a lower alkyl group, a halo lower alkyl group, a hydroxy lower alkyl group, an acyloxy lower alkyl group, a lower alkoxy-lower alkyl group, a lower alkoxy group, a halo lower alkoxy group, a lower alkoxy carbonyl-lower alkoxy group, a lower alkenyloxy group, aralkyloxy group, a lower alkoxy-lower alkoxy group, a lower alkoxycarbonyl group, carboxyl group, carbamoyl group, an N,N-di-lower alkylcarbamoyl group, an N-lower alkyl carbamoyl group, halo group, cyano group, nitro group, hydroxy group, acyloxy group, amino group, a lower alkylsufonylamino group, acylamino group, a lower alkoxycarbonylamino group, acyl group, mercapto group, a lower alkylthio group, a lower alkylsulfinyl group or a lower alkylsulfonyl group (more preferably hydrogen, a lower alkoxy group, aralkyloxy group, a lower alkoxy-lower alkoxy group, hydroxy group or acyloxy group) are preferable and condensed polycyclic hydrocarbon groups represented by the above formula wherein n,$R^4$ and $R^5$ are of the same meaning as defined above, and $R^3$ and $R^6$ are hydrogen are more preferable.

As A, condensed polycyclic hydrocarbon groups represented by the formula:

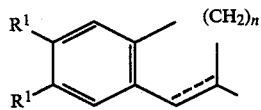

wherein the dotted line designated the presence or absence of double bond (more preferably the presence of double bond), n denotes an integer of 1 to 4 (more preferably 2 or 3) and $R^1$ stands for a lower alkoxy group (more preferably methoxy group or ethoxy group) are further preferable.

As the phenyl group substituted with a lower alkoxy group, represented by R, mention is made of, for example, phenyl groups substituted with one to five lower alkoxy groups, the carbon number of which ranges from about 1 to about 4, such as 2-methoxypenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4-diethoxyphenyl, 3,4-dipropoxyphenyl, 3,4-dibutoxyphenyl, 2,3,4-trimethoxyphenyl, 2,4,5-trimethoxyphenyl, 2,5,6-trimethoxyphenyl, 3,4,5-trimethoxyphenyl, 3,5-dimethoxy-4-ethoxyphenyl, 3,5-dimethoxy-4-propoxyphenyl, 3,5-dimethoxy-4-butoxyphenyl, 2,3,4,5-tetramethoxyphenyl, 2,3,4,5,6-pentamethoxyphenyl, etc.

As R, phenyl groups substituted with three lower alkoxy groups are preferable, phenyl groups represented by the formula

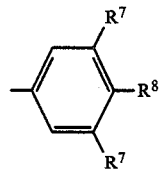

wherein $R^7$ and $R^8$ are independently methoxy group or ethoxy group are more preferably and phenyl groups represented by the above formula wherein at least one of $R^7$ and $R^8$ is methoxy group, and the other is methoxy group or ethoxy group are further preferable. Among other, a phenyl group represented by the formula:

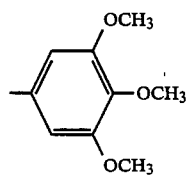

is more preferable.

X stands for methylene group (—$CH_2$—), carbonyl group

or thiocarbonyl group

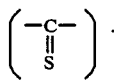

Depending on the value of m, the group

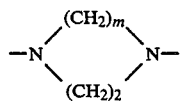

forms a 1,4-piperazinediyl group (m=2) or 1,4-homopiperazinediyl group (m=3). The value of m is preferably 2.

Among the compounds (I), those wherein X is methylene may form salts with an inorganic acid such as hydrogen chloride, hydrobromic acid, sulfuric acid, nitric acid, phosphoric acid, etc. or an organic acid such as acetic acid, tartaric acid, citric acid, fumaric acid, maleic acid, toluenesulfonic acid, methanesulfonic acid, etc., or may form quaternary salts with a lower alkyl halide, the carbon number of the alkyl moiety of which ranges from about 1 to about 4, (e.g. methyl iodide, ethyl iodide, propyl iodide). As the salts of the compounds (I), pharmacologically acceptable ones are preferable, and pharmacologically acceptable acid addition salts are more preferable. Hydrates of the compounds (I) are also usable.

Among the above-mentioned compounds (I), those represented by the formula:

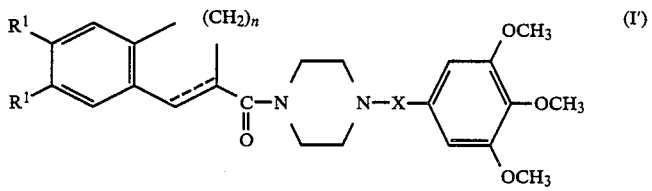

wherein the dotted line designated the presence or absence of double bond (more preferably the presence of double bond), n denotes an integer of 1 to 4 (more preferably 2 or 3), X is of the same meaning as defined above and $R^1$ stands for a lower alkoxy group (more preferably methoxy group or ethoxy group) and their pharmacologically acceptable acid addition salts (in case of X=methylene) are preferable.

The compounds represented by the formula (I) can be produced by, for example, the following four kinds of processes which comprises;

(a) reacting a compound of the formula (III):

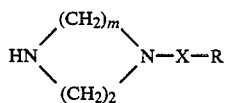

wherein R, X and m are as defined above
with a compounds of the formula (II): A—COOH
wherein A is as defined above,
or a compound of the formula (IV): A—COW
wherein A is as defined above and W is halogen atom
to produce a compound of the formula (I), (b) reacting a compound of the formula (V):

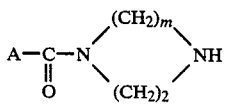

wherein A and m are as defined above
with a compound of the formula (VI): Y—X—R
wherein R is as defined above,
X is methylene group or carbonyl group, and Y is halogen or a group of the formula: $R^aSO_2$—O—
wherein $R^a$ is a lower alkyl, trifluoromethyl, phenyl or p-tolyl, with proviso that when X is carbonyl group, then Y is halogen
to produce a compound of the formula (I)
wherein A, R and m are as defined above and X is methylene group or carbonyl group.

(c) reacting a compound of the formula (V) with a compound of the formula (VII): HOOC—R
wherein R is as defined above
to produce a compound of the formula (I)
wherein A, R and m are as defined above,
and X is carbonyl group,
or (d) reacting a compound of the formula (V) with a compound of the formula (VIII):

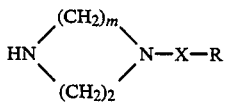

wherein R is defined above under reductive conditions (I')

to produce a compound of the formula (I)
wherein A, R and m are as defined above,
and X is methylene group.

In the process (a) above, the compound (I) of the present invention can be prepared by subjecting a compound represented by the formula:

A—COOH     (II)

wherein A is of the same meaning as defined above and a compound represented by the formula:

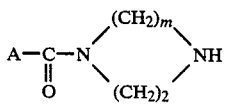     (III)

wherein each symbol is of the same meaning as defined above to dehydrative condensation.

The dehydrative condensation is, for example, a conventional reaction for forming an amide bond. More concretely stating, the dehydrative condensation is carried out by using singly an amide-forming reagent such as dicyclohexylcarbodiimide, N,N'-carbonyldiimidazole, diphenyl phosphoryl azide, diethyl phosphorocyanidate, etc.; or by allowing a compound (II) to react with a compound (III), after converting the compound (II) to an active ester by subjecting a phenol such as 2,4,5-trichlorophenol, pentachlorophenol, pentafluorophenol, 2-nitrophenol or 4-nitrophenol, or an N-hydroxy compound such as N-hydroxysuccinimide, 1-hydroxybentriazole, N-hydroxypiperidine, N-hydroxy-5-norbornene-2,3-dicarboxyimide, etc. to condensation in the presence of a catalyst such as dicyclohexylcarbodiimide, etc., or by allowing a compound (II) to react with a compound (III), after converting the compound (II) to a mixed acid anhydride by allowing it to react with an acid chloride as ethyl chlorocarbonate, isobutyl chlorocarbonate, benzyl chlorocarbonate, etc. This amide-bond forming reaction can be accelerated, either by allowing a compound (II) to react directly with a compound (III) or by allowing a compound (II) to react with a compound (III) after converting the former to its active ester or mixed acid anhydride, by the addition of preferably an organic base such as tertiary amines (e.g. triethylamine, N-methylpiperidine). The reaction temperature ranges usually from about −20° C. to about +50° C., preferably from about −10° C. to about +25° C. Examples of the solvent usually employed include dioxane, tetrahydrofuran, acetonitrile, pyridine, N,N-dimethylformamide, N,N-dimethylacetamide, dimethylsulfoxide, N-methylpyrrolidone, chloroform, methylene chloride, etc., and these may be used singly or as a suitable mixture.

In the process (a) above, the compound (I) of the present invention can also be prepared by allowing a compound represented by the formula:

$$A-COW \qquad (IV)$$

wherein A is of the same meaning as defined above; W stands for a halogen atom to react with a compound (III). This reaction can be allowed to proceed usually in the presence or absence of water or any other organic solvent (e.g. acetonitrile, dimethylformamide, diemthylacetamide, dimethylsulfoxide, tetrahydrofuran, benzene, toluene, ethyl acetate, chloroform, methylene chloride), by keeping the temperature range from about −20° C. to about +150° C. In this case, for the purpose of accelerating the reaction rate, a base such as potassium carbonate, sodium hydroxide, sodium hydrogencarbonate, pyridine, triethylamine, etc. can be allowed to coexist in the reaction system.

In the process (b) above, the compound (I) of the present invention is prepared by allowing a compound represented by the formula:

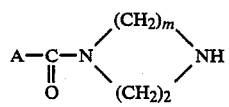

(V)

wherein A and m are of the same meaning as defined above to react with a compound represented by the formula:

$$Y-X-R \qquad (VI)$$

wherein R and X are of the same meaning as defined above, Y stands for halogen (X: methylene group or carbonyl group) or a group represented by the formula $R^aSO_2-O-$ (wherein $R^a$ stands for a lower ($C_{1-4}$) alkyl, trifluoromethyl, phenyl or p-tolyl) (X: methylene group). The reaction can be allowed to proceed in water or any other organic solvent (e.g. acetonitrile, dimethylformamide, dimethylacetamide, dimethylsulfoxide, tetrahydrofuran, acetone, methyl ethyl ketone, benzene, toluene) singly or a suitable admixture, while keeping the temperature ranging from about −20° C. to about +150° C. In this case, a base such as potassium carbonate, sodium hydroxide, potassium hydroxide, pyridine, triethylamine, etc. can be allowed to co-exist in the reaction system.

In the process (c) above, the compound (I) of the present invention, wherein X is carbonyl group, is prepared by allowing a compound (V) and a compound represented by the formula:

$$HOOC-R \qquad (VII)$$

wherein R is of the same meaning as defined above to dehydrative condensation. This dehydrative condensation reaction can be conducted in a manner similar to that of the compound (II) with the compound (III).

And, in the process (d) above, the compound (I) of the present invention, wherein X is methylene group, is prepared by subjecting a compound (V) to condensation under reductive conditions with a compound of the formula:

$$\begin{array}{c} HC-R \\ \parallel \\ O \end{array} \qquad (VIII)$$

wherein R is of the same meaning as defined above.

As the reductive conditions, mention is made of, for example, catalytc reduction using as the catalyst a metal such as platinum, palladium, Raney nickel, rhodium, etc. or a mixture of the metal and an optional carrier (e.g. carbon); reduction by means of a metallic anhydride such as lithium aluminium hydride, lithium borohydride, lithium cyanoborohydride, sodium borohydride, sodium cyanoborohydride, etc.; reduction by means of metallic sodium, metallic magnesium, etc. and alcohols; reduction by means of a metal such as iron, zinc, etc. and an acid such as hydrochloric acid, acetic acid, etc.; electrolytic reduction; reduction by means of reductase; etc. The abovementioned reaction is usually carried out in the presence of water or an organic solvent (e.g. methanol, ethanol, ethyl ether, dioxane, methylene chloride, chloroform, benzene, toluene, acetic acid, N,N-dimethylformamide, N,N-dimethylacetamide), and the reaction temperature varies with the reduction process then employed, but, in general, preferably ranges from about −20° C. to +100° C. This reaction can attain the purpose satisfactorily by carrying out under normal pressure, but it may be conducted, depending on convenience, under elevated or reduced pressure.

The intended compound (I) of the present invention thus obtained can be isolated from the reaction mixture by a conventional separating and purifying means (e.g. extraction, concentration, neutralization, filtration, recrystallization, column chromatography, thin-layer chromatography).

Salts of the compound (I) can be obtained, in some instances, by the reaction per se preparing the compound (I), but, upon necessity, they can be prepared by the addition of an acid or an alkyl halide.

The starting compounds (III), (V) and (VI) can be synthesized by, for example, the following processes (f) to (h).

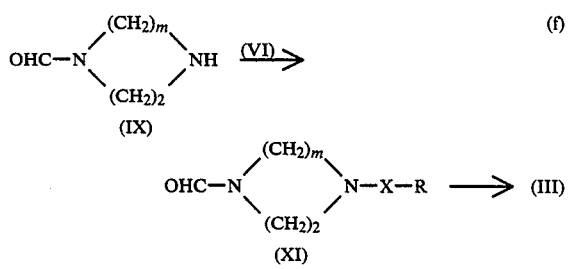

The reaction between the above compounds (IX) and (VI) can be conducted similarly to that between the compounds (V) and (VI). The reaction of the compound (XI) to the compound (III) is deformylation, and it is carried out in water or an organic solvent (e.g. methanol, ethanol, dioxane, tetrahydrofuran, acetonitrile, acetone, dimethylsulfoxide) or a mixture thereof at 0° C. to +100° C. in the presence of an acid (e.g. hydrogen chloride, hydrogen bromide, sulfuric acid) or a base (e.g. potassium hydroxide, sodium hydroxide).

The compounds (III) wherein X is a thiocarbonyl group can be obtained by reacting the compounds (III)

wherein X is carbonyl group with the Lawesson reagent.

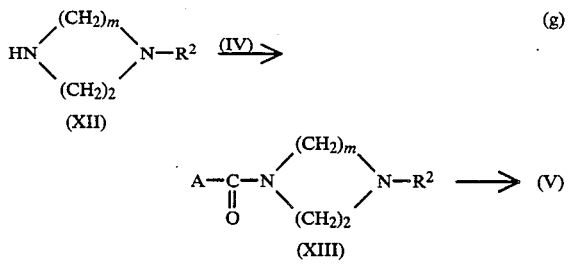

wherein $R^2$ stands for formyl group or benzyl group.

The reaction between the above-mentioned compounds (XII) and (IV) can be conducted in a manner similar to that between the compounds (III) and (IV). The reaction of the compound (XIII) to the compound (V) is deformylation or debenzylation, and the deformylation can be conducted in a manner similar to that of the compound (XI) to the compound (III). The debenzylation can be conducted by catalytic reduction, and the catalytic reduction is conducted in water or an organic solvent (e.g. methanol, ethanol, ethyl acetate, dioxane, tetrahydrofuran) or a mixture thereof in the presence of a suitable catalyst such as palladium-carbon. This reaction is conducted under normal pressure to about 150 kg/cm² at temperatures ranging from 0° C. to +150° C., and, for accelerating the reaction rate, an acid (e.g. hydrogen chloride, hydrogen bromide, hydrogen fluoride, sulfuric acid) may be added to the reaction system.

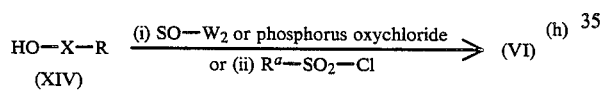

wherein W is of the same meaning as defined above.

The above reaction (i) is conducted in a suitable organic solvent (e.g. benzene, toluene, ether) at temperatures ranging from about 0° C. to about +120° C. in the presence or absence of a base (e.g. pyridine, dimethylaniline, triethylamine) (X=carbonyl group or methylene group). The above reaction (ii) is conducted in a suitable organic solvent (e.g. benzene, toluene, ether) at temperatures ranging from about −20° C. to about +25° C. in the presence of a base (e.g. pyridine) (X=methylene group). Incidentally, the reaction can be conducted using a base as the solvent.

And, the compound (IV) can be obtained by subjecting the compound (II) as the starting compound to a reaction similar to that of the reaction (i) of the compound (XIV) to the compound (VI).

The compound (II) can easily be synthesized by a method described on literature references [e.g. Jacques et al., Bull. Soc. Chim. Fr., 512 (1950); Hashem et al., J. Med. Chem., 19, 229 (1976); Itoh et al., Chem. Pharm. Bull., 26, 504 (1978); Miyake et al., Chem. Pharm. Bull., 31, 2329 (1983); Itoh et al., Chem. Pharm. Bull. 32, 130 (1984); Tamura et al., J. Agr. Chem. Soc. Japan 27, 318 (1953); Organic Syntheses, 26, 28 (1949)] or methods analogous thereto. For example, when the compound (II) is a compound represented by the formula:

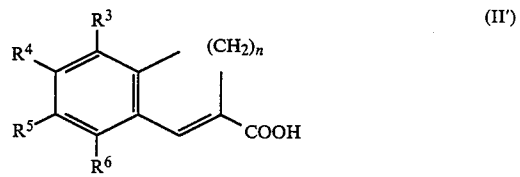

wherein each symbol is of the same meaning as defined above, it can be easily synthesized in accordance with the following reaction schema.

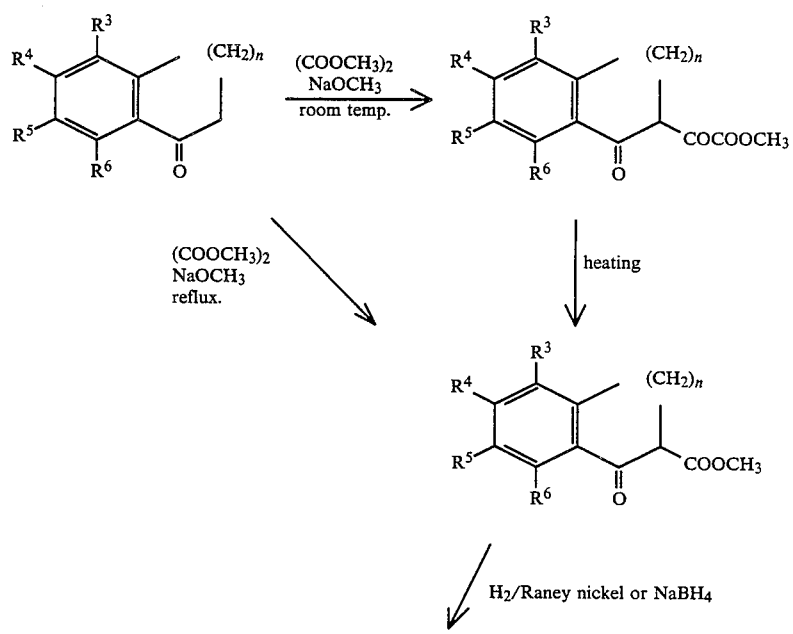

-continued

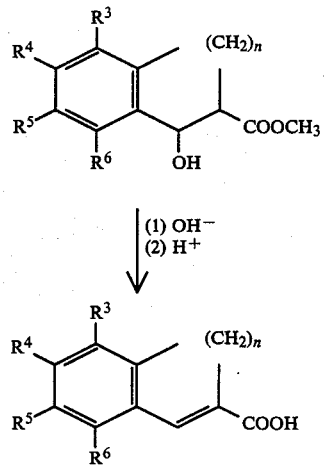

The compound (I) and salts thereof exhibit excellent PAF antagonism and are useful as prophylactic and therapeutic agents of circulatory disturbances due to PAF, for example, thrombosis, apoplexy (e.g. cerebral hemorrahge, cerebral thrombosis), myocardial infarction, angina pectoris, venous thrombosis, nephritis (e.g. gluomerulonephritis), diabetic nephritides, shock (e.g. endotoxin chock observed after grave infectious diseases or postoperative shock, intravascular hemagglutination syndrome, anaphylactic shock, hemorrhagic shock); gastroenteric diseases causes by PAG (e.g. gastric ulcer); diseases associated with allergy and inflammation (e.g. bronchial asthma, psoriasis); pneumonia; rejection symptoms associated with increase in the amount of PAF produced in the case of internal organ transplantation; insufficiency of internal organs (e.g. heart, liver, kidney) in the case of internal organ operation. The compound (I) and salts thereof are low in toxicity, and can therefore be administered orally or non-orally as they are in a form of power or as a pharmaceutical composition in a suitable dosage form, to mammals (e.g. man, rabbit, dog, cat, rat, mouse). The dosage varies depending upon the subject to be administered, disease to be treated, conditions thereof and route of administration, and when the compound (I) or a salt thereof is used for prophylaxis or therapy of shock in a human adult, it is convenient to administer through intravenous injection usually in a single dose in the range of from about 0.01 to about 20 mg/kg body weight, preferably in the range of from about 0.1 to about 10 mg/kg body weight, more preferably in the range of from about 0.1 to about 2 mg/kg body weight, about once to five times a day, preferably about once to three times a day. And, the compound (I) and salts thereof can be administered through drip injection in a single dose in the range of from about 0.01 to about 1.0 mg/kg body weight/min for one hour, about once to five times a day, preferably once to three times a day. The dosages for other non-oral routes as well as the oral dosage may be selected referring to the above-mentioned dose levels. When shock symptoms are very serious, dosage may be increased depending on the symptoms.

When the compound (I) or a salt thereof is used orally for the prophylaxis or therapy of, for example, thrombosis, bronchial asthma, nephritis, etc. in a human adult, it is convenient to administer usually in a single dose in the range of from about 0.05 to about 20 mg/kg body weight, preferably in the range from about 0.2 to about 5 mg/kg body weight, about once to five times a day, preferably from once to three times. The dosages for other non-oral routes may be selected referring to the above-mentioned dose levels.

The pharmaceutical composition can be used for the above administration comprises an effective amount of the compound (I) or a salt thereof and a pharmaceutically acceptable carrier or excipient, and the said composition is provided in a dosage form suitable for oral or non-oral administration.

The composition for oral administration includes, for example, solid or liquid dosage forms, and as their specific examples, there may be mentioned tablets (inclusive of sugar-coated tablets and film-coating tablets), pills, granules, powders, capsules (inclusive of soft capsules), syrups, emulsions, suspensions, etc. Such compositions can be manufactured by per se known procedures and comprise carriers and excipients commonly used in the pharmaceutical industry. Examples of the carriers and excipients for the preparation of tablets include lactose, starch, sugar and magnesium stearate, etc.

The compositions for non-oral administration include, for example, injections, ointments, fomentations, paints and suppositories, and as examples for injectables, there may be mentioned dosage forms, such as injectable solutions for intravenous injection, for subcutaneous injection, for intracutaneous injection, for intramuscular injection and for drip injection. Such injectable solutions are prepared by per se known procedures, for example, by dissolving, suspending or emulsifying the compound (I) or a salt thereof in a sterile aqueous or oily solution usually used for injectable solutions. The aqueous solution for injection includes, for example, physiological saline solution, isotonic solution containing glucose and other adjuvants, and may be employed in combination with a suitable solubilizer, such as alcohols (e.g. ethanol), polyalcohols (e.g. propylene glycol, polyethylene glycol), and nonionic surface active agents [e.g. polysorbate 80, HCO-50 (polyoxyethylene (50 mol) adduct of hydrogenated castor oil)], etc. The oily solution includes, for example, sesame oil and soybean oil, and may be used in combination with such a solubilizer as benzyl benzoate and benzyl alcohol. The injectable solution prepared is usually filled into suitable ampoules to be supplied as an injection. The suppositories for rectal administration are prepared by a per se known procedure, for example, by incorporating the compound (I) or a salt thereof into a conventional base material for suppository use, followed by moulding.

The above-mentioned compositions may contain any other active components, so long as they do not cause undesirable interactions by the incorporation with the compound (I) or a salt thereof. For example, to mammals suffering from infectious diseases, an antibiotic may be administered together with the compound (I) or a salt thereof for preventing endotoxin-shock.

The compounds (I) of the present invention and their salts are excellent in absorption from the intestinal canal and show excellent PAF antagonism even by oral administration. Therefore, the compounds (I) and their salts can be administered not only non-orally such as be injection, but also orally.

EXAMPLES

The following working examples are given to illustrate the present invention more concretely, but it is not to be limited thereto.

EXAMPLE 1

A mixture of 7-methoxy-1,2-dihydro-3-naphthoic acid [Jacques et al., Bull. Soc. Chim. Fr., 512 (1950)] (2 g), benzene (50 ml) and thionyl chloride (2 ml) is heated under reflux for one hour. After distilling off the solvent under reduced pressure, benzene (50 ml) is added and the benzene is distilled off again under reduced pressure. The 7-methoxy-1,2-dihydro-3-naphthoyl chloride thus obtained is dissolved in dioxane (10 ml). The solution is added dropwise to a mixture of 1-(3,4,5-trimethoxybenzyl)piperazine dihydrochloride (2.6 g), dioxane (50 ml) and triethylamine (5 ml) at room temperature with stirring. Then the mixture is stirred at room temperature for 30 minutes. Water (300 ml) is added to the mixture, which is extracted with ethyl acetate. The extract solution is washed with a dilute aqueous solution of sodium hydroxide and water, then the solvent is distilled off under reduced pressure. The resulting oily substance is purified by silica gel column chromatography (hexane:acetone=1:1). The product thus obtained is dissolved in ethanol and the solution is treated with on ethanolic hydrogen chloride (5 ml) to give 1-(7-methoxy-1,2-dihydro-3-naphthoyl)-4-(3,4,5-trimethoxybenzyl)piperazine hydrochloride (2.9 g) as colorless crystals, m.p. 210°–215° C. (decomp.).

Elemental Analysis for $C_{26}H_{32}N_2O_5.HCl$: Calcd.: C 63.86; H 6.80; N 5.73. Found: C 63.66; H 6.88; N 5.62.

EXAMPLE 2

Diethyl phosphorocyanidate (1.2 ml) is added dropwise to a mixture of 7,8-dimethoxy-1,2-dihydro-4-naphthoic acid (0.5 g), 1-(3,4,5-trimethoxybenzyl)piperazine dihydrochloride (0.87 g), triethylamine (0.86 g) and N,N-dimethylformamide (20 ml) with stirring. After stirring for one hour at room temperature, water (100 ml) is added to the reaction mixture and the mixture is extracted with ethyl acetate (100 ml). The organic layer is washed with water, dried and concentrated under reduced pressure. The resulting oily substance is purified by silica gel column chromatography (hexane:acetone=1:1). The product thus obtained is dissolved in ethyl ether and the solution is treated with 5N ethanolic hydrogen chloride (2 ml) to give 1-(7,8-dimethoxy-1,2-dihydro-4-naphthoyl)-4-(3,4,5-trimethoxybenzyl)piperazine hydrochloride (0.75 g) as colorless powder.

Elemental Analysis for $C_{27}H_{34}N_2O_6.HCl.H_2O$: Calcd.: C 60.38; H 6.94; N 5.22. Found: C 60.25; H 6.79; N 5.10.

EXAMPLE 3

A mixture of 7-methoxy-1,2-dihydro-3-naphthoic acid (0.22 g), 5% palladium-carbon (0.1 g) and methanol (20 ml) is subjected to catalytic reduction at room temperature under atmospheric pressure of $H_2$. After hydrogen absorption has ceased, the catalyst is filtered off, and the filtrate is evaporated to dryness under reduced pressure to give 6-methoxy-1,2,3,4-tetrahydro-2-naphthoic acid as colorless powder. To this product are added 1-(3,4,5-trimethoxybenzyl)piperazine dihydrochloride (0.4 g), triethylamine (0.5 g) and N,N-dimethylformamide (10 ml), and the mixture is stirred. To this solution is added dropwise at room temperature diethyl phosphorocyanidate (1 ml). The mixture is stirred for one hour. After addition of water (100 ml), the reaction mixture is extracted with ethyl acetate. The organic layer is washed with water, dried and concentrated under reduced pressure. The residue is purified by silica gel column chromatography (hexane:acetone=1:1). The resulting oily product is dissolved in ethanol and the solution is treated with 5N ethanolic hydrogen chloride (1 ml). The mixture is diluted with ethyl ether, and then resulting precipitates are collected by filtration to give 1-(6-methoxy-1,2,3,4-tetrahydro-2-naphthoyl)-4-(3,4,5-trimethoxybenzyl) piperazine hydrochloride (0.35 g) as colorless prisms, m.p. 220°–225° C. (decomp.).

Elemental Analysis for $C_{26}H_{34}N_2O_5.HCl$: Calcd.: C 63.60; H 7.18; N 5.71. Found: C 63.56; H 7.20; N 5.72.

EXAMPLE 4

6,7-Dimethoxy-1-oxo-1,2,3,4-tetrahydro-2-naphthoic acid methyl ester [Hashem et al., J. Med. Chem., 19, 229 (1976)] (14 g) is dissolved in a mixture of methylene chloride (200 ml) and methanol (200 ml). Sodium borohydride (1 g) is added to the solution with stirring at room temperature, and the mixture is then stirred for one hour. The resulting mixture is supplemented with sodium borohydride (1 g) and the mixture is stirred for 30 minutes. To the resultant is then further added sodium borohydride (0.5 g) and the mixture is stirred for 30 minutes. After addition of water (500 ml) to the mixture, the methylene chloride layer is separated. The aqueous layer is extracted with methylene chloride (200 ml). The extracts are combined and concentrated under reduced pressure to give the methyl ester of 6,7-dimethoxy-1-hydroxy-1,2,3,4-tetrahydro-2-naphthoic acid. This product is dissolved in methanol (10 ml), and an aqueous solution (100 ml) of sodium hydroxide (14 g) is added dropwise to the solution at room temperature with stirring. After finishing the dropwise addition, the mixture is allowed to stand at room temperature for 30 minutes. Water (200 ml) is added to the mixture, and the mixture is extracted with a mixture of ethyl ether (100 ml) and petroleum ether (100 ml). The aqueous layer is made acid with concentrated hydrochloric acid and extracted with methylene chloride (300 ml). The extract is washed with water, dried and concentrated under reduced pressure. To the residue are added dioxane (100 ml) and concentrated hydrochloric acid (10 ml), and the mixture is heated at 80° C. for 5 minutes. The reaction mixture is concentrated under reduced pressure to half of its original volume. To the concentrate is added an aqueous solution (200 ml) of sodium hydroxide (10 g).

The mixture is extracted with a mixture of ether (50 ml) and petroleum (50 ml). The aqueous layer is made acid with concentrated hydrochloric acid, and then precipitating colorless prisms are collected by filtration to give 1,2-dihydro-6,7-dimethoxy-3-naphthoic acid (6.2 g), m.p. 191°–194° C.

Elemental Analysis for $C_{13}H_{14}O_4$: Calcd.: C 66.66; H 6.02. Found: C 66.38; H 6.14.

[Incidentally, this product can be synthesized also by the method disclosed in Org. Syntheses, 26, 28 (1946).]

EXAMPLE 5

A mixture of 6,7-dimethoxy-1,2-dihydro-3-naphthoic acid (15 g), toluene (100 ml) and thionyl chloride (20 ml) is refluxed for one hour. The reaction is concentrated under reduced pressure. To the residue is added toluene (50 ml) and the mixture is again concentrated under reduced pressure. Thus-obtained 6,7-dimethoxy-1,2-dihydro-3-naphthoyl chloride is dissolved in N,N-dimethylformamide (20 ml). The solution is added dropwise to a mixture of 1-(3,4,5-trimethoxybenzyl)piperazine dihydrochloride (22.9 g), N,N-dimethylformamide (80 ml) and triethylamine (25 ml), over a period of 5 minutes under ice-cooling with stirring. Then, the mixture is stirred at room temperature for 2 hours. After addition of an excess volume of water, the mixture is extracted with ethyl acetate. The extract is washed with water, dried and concentrated under reduced pressure. A solution of the residue dissolved in ethyl acetate (100 ml) and ethanol (50 ml) is treated with 5N ethanolic hydrogen chloride (20 ml). The resulting precipitates are collected by filtration and washed with ethanol. Thus-obtained precipitates (22.3 g) are recrystallized from methanol (250 ml) to afford 1-(6,7-dimethoxy-1,2-dihydro-3-naphthoyl)-4-(3,4,5-trimethoxybenzyl)piperazine hydrochloride (17.5 g) as colorless crystals. Mother liquor portions are combined and concentrated under reduced pressure, and the concentrate is neutralized and extracted with ethyl acetate. The extract solution is concentrated under reduced pressure. The residue is purified by silica gel column chromatography (acetone:ethyl acetate:hexane=2:2:1), followed by leading to hydrochloride to further yield the product (4.3 g). The overall yield is 21.8 g. Melting point: 215°–220° C. (decomp.).

Elemental Analysis for $C_{27}H_{34}N_2O_6 \cdot HCl$: Calcd.: C 62.48; H 6.80; N 5.40. Found: C 62.40; H 6.85; N 5.31.

EXAMPLE 6

Diethyl phosphorocyanidate (1 ml) is added dropwise, under ice-cooling, to a mixture of 1,2-dihydro-6,7-dimethoxy-3-naphthoic acid (0.8 g), 1-(3,4,5-trimethoxybenzyl)piperazine dihydrochloride (1 g), triethylamine (0.35 g) and N,N-dimethylformamide (30 ml). The whole mixture is stirred for one hour under ice-cooling and allowed to stand at room temperature for one hour. Water (100 ml) is added to the reaction mixture and the mixture is extracted with ethyl acetate (100 ml). The organic layer is washed with water, dried and concentrated under reduced pressure. The residue is purified silica gel column chromatography (hexane:acetone=1:1–1:2). The oily product thus obtained is treated with hydrogen chloride is ethyl acetate to afford 1-(6,7-dimethoxy-1,2-dihydro-3-naphthoyl)-4-(3,4,5-trimethoxybenzyl)piperazine hydrochloride, which is identical with the product obtained in Example 5. The yield is 0.85 g.

Example 7

Using 1-(3,4,5-trimethoxybenzyl)piperazine (0.5 g), 2-naphthoic acid (0.48 g), triethylamine (0.2 g), N,N-dimethylformamide (20 ml) and diethyl phosphorocyanidate (0.6 ml), an amidation as that described in Example 6 is carried out. The product is purified by silica gel column chromatography (hexane:acetone=2:1) and converted to the hydrochloride to give 1-(2-naphthoyl)-4-(3,4,5-trimethoxybenzyl)piperazine hydrochloride (0.5 g) as colorless crystals, m.p. 198°–205° C. (decomp.).

Elemental Analysis for $C_{25}H_{28}N_2O_4 \cdot HCl$: Calcd.: C 65.71; H 6.40; N 6.13. Found: C 65.27; H 6.40; N 6.09.

EXAMPLE 8

Using 1-(3,4,5-trimethoxybenzyl)piperazine (0.5 g), 1-naphthoic acid (0.48 g), triethylamine (0.2 g), N,N-dimethylformamide (20 ml) and diethyl phosphorocyanidate (0.6 ml), an amidation as that described in Example 6 is carried out. The product is purified by silica gel column chromatography (hexane:acetone=2:1) and converted to the hydrochloride to give 1-(1-naphthoyl)-4-(3,4,5-trimethoxybenzyl)piperazine hydrochloride (0.6 g) as colorless crystals, m.p. 170°–173° C.

Elemental Analysis for $C_{25}H_{28}N_2O_4 \cdot HCl \cdot \frac{1}{2}H_2O$: Calcd.: C 64.43; H 6.49; N 6.01. Found: C 63.93; H 6.37; N 5.97.

EXAMPLE 9 using 6-methoxy-2-naphthoic acid (0.3 g), 1-(3,4,5-trimethoxybenzyl)piperazine (0.5 g), triethylamine (0.2 g), N,N-dimethylformamide (20 ml) and diethyl phosphorocyanidate (0.6 ml), an amidation as that described in Example 6 is carried out. The product is purified by silica gel column chromatography (hexane:acetone=4:3) and led in ethyl ether to the hydrochloride to give a white powder, followed by recrystallization from a mixture of ethyl acetate and ethyl ether to afford 1-(6-methoxy-2-naphthoyl)-4-(3,4,5-trimethoxybenzyl)piperazine hydrochloride (0.35 g) as colorless crystals, m.p. 169°–173° C.

Elemental Analysis for $C_{26}H_{30}N_2O_5 \cdot HCl \cdot H_2O$: Calcd.: C 61.83; H 6.59; N 5.55. Found: C 62.10; H 6.52; N 5.49.

EXAMPLE 10

Using 6,7,8-trimethoxy-1,2-dihydro-3-naphthoic acid (0.53 g), 1-(3,4,5-trimethoxybenzyl)piperazine (0.53 g), triethylamine (0.2 g), N,N-dimethylformamide (20 ml) and diethyl phosphorocyanidate (0.6 ml), an amidation as that described in Example 6 is carried out. The product is purified by silica gel column chromatography (hexane:acetone=1:1) and then converted to the hydrochloride in ethyl ether. The colorless powder thus obtained is recrystallized from a mixture of ethyl acetate and ethyl ether to afford 1-(6,7,8-trimethoxy-1,2-dihydro-3-naphthoyl)-4-(3,4,5-trimethoxybenzyl)piperazine hydrochloride (0.8 g) as colorless crystals, m.p. 203°–206° C. (decomp.).

Elemental Analysis for $C_{28}H_{36}N_2O_7 \cdot HCl \cdot \frac{1}{2}H_2O$: Calcd.: C 60.26; H 6.86; N 5.02. Found: C 60.27; H 6.81; N 4.90.

EXAMPLE 11

A mixture of 6,7,8-trimethoxy-1,2-dihydro-3-naphthoic acid (1 g) and powdery sulfur (0.25 g) is heated at 220° C. for 15 minutes. After cooling, the reaction mixture is dissolved in ethanol. Insolubles are filtered off, and the filtrate is concentrated under reduced pressure. The residue is recrystallized from ethyl ether to give 5,6,7-trimethoxy-2-naphthooic acid as colorless prisms (0.65 g), m.p. 180°-182° C.

Elemental Analysis for $C_{14}H_{14}O_5$: Calcd.: C 64.12; H 5.38. Found: C 63.69; H 5.40.

EXAMPLE 12

Using 5,6,7-trimethoxy-2-naphthoic acid (0.55 g), 1-(3,4,5-trimethoxybenzyl)piperazine (0.6 g), triethylamine (0.2 g), N,N-dimethylformamide (20 ml) and diethyl phosphorocyanidate (0.6 ml), an amidation as that described in Example 6 is carried out. The product is purified by silica gel column chromatography (hexane:acetone=1:1) and converted to the hydrochloride, followed by crystallization from a mixture of ethyl acetate and ethyl ether to thereby afford 1-(3,4,5-trimethoxybenzyl)-4-(5,6,7-trimethoxy)-2-naphthoyl)piperazine hydrochloride (0.8 g) as colorless crystals, m.p. 194°-198° C.

Elemental Analysis for $C_{28}H_{34}N_2O_7.HCl.\frac{1}{2}H_2O$: Calcd.: C 60.48; H 6.53; N 5.04. Found: C 60.57; H 6.45; N 5.03.

EXAMPLE 13

Using 6,7,8-trimethoxy-1,2-dihydro-3-naphthoic acid (0.67 g), 1-(2,3,4-trimethoxybenzyl)piperazine dihydrochloride (0.77 g), triethylamine (1 g), N,N-dimethylformamide (20 ml) and diethyl phosphorocyanidate (0.7 ml), an amidation as that described in Example 6 is carried out. The product is purified by silica gel column chromatography (hexane:acetone=2:1) and converted to the hydrochloride in a mixture of ethyl acetate and ethyl ether to thereby obtain 1-(2,3,4-trimethoxybenzyl)-4-(6,7,8-trimethoxy-1,2-dihydro-3-naphthoyl)piperazine hydrochloride (1 g) as colorless needles, m.p. 180°-185° C.

Elemental Analysis for $C_{28}H_{36}N_2O_7.HCl.H_2O$: Calcd.: C 59.31; H 6.93; N 4.94. Found: C 59.21; H 6.67; N 4.79.

EXAMPLE 14

Powdery sodium methoxide is prepared by subjecting a 28% methonol solution of sodium methoxide to concentration to dryness under reduced pressure. To this product is added a mixture of 6-butoxy-3,4-dihydro-1 (2H)-naphthalenone [Miyake et al., Chem. Pharm. Bull., 31, 2329 (1983)] (19 g), dimethyl oxalate (20.5 g) and benzene (100 ml) and the mixture is stirred at room temperature for one hour and then allowed to stand overnight. To the reaction mixture are added ethyl acetate (200 ml) and water (200 ml). The reaction mixture is acidified with concentrated hydrochloric acid. The ethyl acetate layer is separated, washed with water, dried and concentrated under reduced pressure. The residue is crystallized from a mixture of ethyl ether and petroleum ether to afford methyl 2-(6-butoxy-1-oxo-1,2,3,4-tetrahydro-2-naphthyl)-2-oxoacetate (15.5 g) as pale yellow needles, m.p. 70°-71° C.

Elemental Analysis for $C_{17}H_{20}O_5$: Calcd.: C 67.09; H 6.62. Found: C 66.98; H 6.59.

A mixture of this product (15 g) and glass powder (4 g) is stirred at 190° C. for 30 minutes. After cooling, ethyl acetate (200 ml) is added to the reaction mixture. The insolubles are filtered off, and the filtrate is concentrated under reduced pressure. The oily product thus-obtained is dissolved in methanol (100 ml), and 0.5 g each portion of sodium borohydride is added to the solution four times at intervals of 30 minutes under ice-cooling and with stirring, followed by stirring for 30 minutes. To the mixture are added water (500 ml), ethyl acetate (200 ml) and hexane (100 ml), and the mixture is shaken thoroughly. The organic layer is separated washed with water, dried and concentrated under reduced pressure. The oily product thus-obtained is purified by silica gel column chromatography (hexane:ethyl acetate=2:1). The product is crystallized from a mixture of ethyl ether and petroleum ether to afford 6-butoxy-1-hydroxy-1,2,3,4-tetrahydro-2-naphthoic acid methyl ester (3.3 g) as colorless needles (3.3 g), m.p. 81°-83° C.

Elemental Analysis for $C_{16}H_{22}O_4$: Calcd.: C 69.04; H 7.97. Found: C 69.05; H 7.95.

This product (3.3 g) is added to a mixture of methanol (50 ml), water (30 ml) and sodium hydroxide (3 g) and the mixture is heated for one hour under reflux. The reaction mixture is concentrated under reduced pressure, and the concentrate is made acid with concentrated hydrochloric acid, then precipitating crystals are collected by filtration. This product is dissolved in a mixture of dioxane (50 ml), concentrated hydrochloric acid (2 ml) and water (8 ml). The solution is heated at 80° C. for 5 minutes, followed by concentration under reduced pressure. To the residue is added water, and the precipitating crystals are collected by filtration, followed by recrystallization from a mixture of acetone and water to afford 7-butoxy-1,2-dihydro-3-naphthoic acid as colorless needles (2.6 g), m.p. 148°-150° C.

Elemental Analysis for $C_{15}H_{18}O_3$: Calcd.: C 73.15; H 7.37. Found: C 73.11; H 7.36.

EXAMPLE 15

Using 7-butoxy-1,2-dihydro-3-naphthoic acid (0.7 g), 1-(3,4,5-trimethoxy)piperazine dihydrochloride (0.96 g), treithylamine (1.1 g), N,N-dimethylformamide (20 ml) and diethyl phosphorocyanidate (0.7 ml), an amidation as that described in Example 6 is carried out. The product is purified by silica gel column chromatography (hexane:acetone=2:1-1:1), and converted to the hydrochloride in a mixture of ethyl acetate and ethyl ether to thereby give 1-(7-butoxy-1,2-dihydro-3-naphthoyl)-4-(3,4,5-trimethoxybenzyl)piperazine hydrochloride (0.9 g) as colorless prisms, m.p. 193°-196° C. (decomp.).

Elemental Analysis for $C_{29}H_{38}N_2O_5.HCl$: Calcd.: C 65.59; H 7.40; N 5.27. Found: C 65.61; H 7.45; N 5.17.

EXAMPLE 16

A mixture of 7-butoxy-1,2-dihydro-3-naphthoic acid (0.9 g) and powdery sulfur (0.25 g) is heated at 200°-210° C. for 35 minutes. After cooling, the mixture is dissolved in ethyl ether (200 ml). The solution is extracted with a 0.5N aqueous solution of sodium hydroxide. The aqueous layer is made acid with concentrated hydrochloric acid, and the precipitating crystals are collected by filtration. The crystals are dissolved in acetone, and insolubles are filtered off. The filtrate is concentrated under reduced pressure to allow crystals to precipitate. To the precipitates is added (100 ml), and the precipitates are collected by filtration to afford 6-butoxy-2-naphthoic acid (0.6 g) as pale brown powdery crystals, m.p. 175°-180° C.

EXAMPLE 17

Using 6-butoxy-2-naphthoic acid (0.5 g), 1-(3,4,5-trimethoxybenzyl)piperazine dihydrochloride (0.7 g), triethylamine (0.85 g), N,N-dimethylformamide (20 ml) and diethyl phosphorocyanidate (0.5 ml), an amidation as that described in Example 6 is carried out. The reaction mixture is purified by silica gel column chromatography (hexane:acetone=3:2). The product is converted to the hydrochloride in a mixture of ethyl acetate and ethyl ether to afford 1-(6-butoxy-2-naphthoyl)-4-(3,4,5-trimethoxybenzyl)piperazine hydrochloride (0.7 g) as colorless prisms, m.p. 185°–190° C. (decomp.).

Elemental Analysis for $C_{29}H_{36}N_2O_5 \cdot HCl \cdot \frac{1}{2}H_2O$: Calcd.: C 64.73; H 7.12; N 5.21. Found: C 64.72; H 7.08; N 5.03.

EXAMPLE 18

A mixture of 5,6-dimethoxy-1-indanone (5 g), powdery sodium methoxide (obtained by subjecting a 28% methanol solution of sodium methoxide (21 g) to concentration to dryness under reduced pressure) and diethyl carbonate (60 ml) is heated under reflux for 5 hours in a stream of nitrogen. The reaction mixture is cooled. Water and dilute hydrochloric acid are added to the mixture. The acidic mixture is extracted with ethyl acetate. The extract solution is washed with water, dried and concentrated under reduced pressure. The crystals are collected by filtration to give methyl ester of 5,6-dimethoxy-1-oxo-2-indane carboxylic acid (5.7 g), m.p. 162°–163° C. (colorless needles: recrystallized from ethanol).

Elemental Analysis for $C_{13}H_{14}O_5$: Calcd.: C 62.39; H 5.64. Found: C 62.32; H 5.63.

This product (5 g) is dissolved in a mixture of methylene chloride (50 ml) and methanol (50 ml). The the solution is added sodium borohydride (0.9 g) in limited amounts. To the reaction mixture is added water, and the methylene chloride layer separated. The aqueous layer is extracted with methylene chloride. The organic layers are combined, washed with water, dried and concentrated under reduced pressure to leave methyl ester of 5,6-dimethoxy-1-hydroxy-2-indane carboxylic acid, which is dissolved in methanol (4 ml). The the solution is added dropwise an aqueous solution (25 ml) of sodium hydroxide (5 g). The mixture is stirred for 30 minues at room temperature and added water (100 ml), followed by extraction with ethyl ether. The aqueous layer is made acid with hydrochloric acid, and extracted with ethyl acetate. The extract solution is concentrated under reduced pressure. To the residue are added dioxane (40 ml) and concentrated hydrochloric acid (5 ml), and the mixture is heated at 80°–90° C. for 15 minutes. The reaction mixture is concentrated under reduced pressure. To the residue is added an aqueous solution (50 ml) of sodium hydroxide (5 g). The mixture is extracted with ethyl ether. The aqueous layer is made acid with hydrochloric acid, and precipitating crystals are collected by filtration to give 5,6-dimethoxy-1H-indene-2-carboxylic acid (1.5 g), m.p. 251°–252° C. (yellow needles: recrystallized from ethyl acetate).

Elemental Analysis for $C_{12}H_{12}O_4$: Calcd.: C 65.45; H 5.49. Found: C 65.19; H 5.52.

EXAMPLE 19

Diethyl phosphorocyanidate (0.9 g) is added dropwise to an ice-cooling mixture consisting of 5,6-dimethoxy-1H-indene-2-carboxylic acid (0.8 g), 1-(3,4,5-trimethyoxybenzyl)piperazine dihydrochloride (1.3 g), triethylamine (2 ml) and N,N-dimethylformamide (12 ml) with stirring. The whole mixture is stirred at room temperature for two hours and water is added. The mixture is extracted with ethyl acetate. The extract solution is washed with water, dried and then concentrated under reduced pressure. The residue is purified by silica gel column chromatography (ethyl acetate:hexane:acetone=12:8:5) to give an oily product. This product is converted to the hydrochloride in ethanol to afford 1-(5,6-dimethoxy-1H-inden-2-ylcarbonyl)-4-(3,4,5-trimethoxybenzyl)piperazine hydrochloride (1.45 g) as colorless scales, m.p. 245°–250° C. (decomp.).

Elemental Analysis for $C_{26}H_{32}N_2O_6 \cdot \frac{1}{2}H_2O$: Calcd.: C 60.75; H 6.67; N 5.45. Found: C 60.80; H 6.66; N 5.44.

EXAMPLE 20

A mixture of 6,7-dimethoxy-1,2-dihydro-3-naphthoic acid (1.7 g) and powdery sulfur (0.47 g) is heated at 215° C. for 30 minutes to afford 6,7-dimethoxy-2-naphthoic acid (1.6 g), which is recrystallized from ethanol to give colorless prisms, m.p. 245°–247° C.

Elemental Analysis for $C_{13}H_{12}O_4$: Calcd.: C 67.23; H 5.21. Found: C 67.34; H 5.39.

EXAMPLE 21

Using 6,7-dimethoxy-2-naphthoic acid (0.7 g), 1-(3,4,5-trimethoxybenzyl)piperazine dihydrochloride (1.1 g), triethylamine (1.25 g), N,N-dimethylformamide (20 ml) and diethyl phosphorocyanidate (1 ml), an amidation as that described in Example 6 is carried out. The product is purified by silica gel column chromatography (hexane:acetone=2:3) and converted to the hydrochloride in ethyl acetate to give 1-(6,7-dimethoxy-2-naphthoyl)-4-(3,4,5-trimethoxybenzyl)piperazine hydrochloride (1.25 g) as colorless crystals, m.p. 235°–240° C. (decomp.).

Elemental Analysis for $C_{27}H_{32}N_2O_6 \cdot HCl \cdot \frac{1}{2}H_2O$: Calcd.: C 61.65; H 6.51; N 5.33. Found: C 61.55; H 6.46; N 5.27.

Example 22

A mixture of 6,7-dimethoxy-2-naphthoic acid (0.5 g), acetic acid (5 ml) and hydrobromic acid (47%) (10 ml) is heated under reflux for one hour. The reaction mixture is concentrated to dryness under reduced pressure, and a 5N ethanolic hydrogen chloride solution (50 ml) is added to the residue. the whole mixture is left standing overnight at room temperature. The resultant is concentrated to dryness under reduced pressure. N,N-dimethylformamide (10 ml), potassium carbonate (5 g), potassium iodide (0.5 g) and butyl chloride (4 ml) are added to the residue, and the mixture is stirred at 100° C. for 3 hours. After cooling, water is added to the mixture. The mixture is extracted with a solution of ethyl acetate-hexane (1:1). The extract solution is washed with water, dried and concentrated under reduced pressure. The residue is purified by silica gel column chromatography (hexane:ethyl acetate=20:1) to give methyl ester of 6,7-dibutoxy-2-naphthoate (0.35 g) as pale yellow powder.

A mixture of this product (0.35 g), methanol (50 ml), water (5 ml) and sodium hydroxide (1 g) is refluxed for

---

Elemental Analysis for $C_{15}H_{16}O_3$: Calcd.: C 73.75; H 6.60. Found: C 73.30; H 6.82.

one hour. After cooling, water (100 ml) is added to the reaction mixture and the mixture is extracted with petroleum ether (50 ml). the aqueous layer is made acid with hydrochloric acid and the resulting precipitates are collected by filtration to give 6,7-dibutoxy-2-naphthoic acid (0.28 g) as pale yellow needles, m.p. 168°–169° C.

Elemental Analysis for $C_{19}H_{24}O_4$: Calcd.: C 72.13; H 7.65. Found: C 72.21; H 7.71.

EXAMPLE 23

Using 6,7-dibutoxy-2-naphthoic acid (0.25 g), 1-(3,4,5-trimethoxybenzyl)piperazine dihydrochloride (0.31 g), triethylamine (0.35 g), N,N-dimethylformamide (10 ml) and diethyl phosphorocyanidate (0.5 ml), an amidation as that described in Example 6 is carried out. The reaction mixture is purified by gel column chromatography (hexane:acetone=1:1) and converted to the hydrochloride in ethyl acetate to give 1-(6,7-dibutoxy-2-naphthoyl)-4-(3,4,5-trimethoxybenzyl)piperazine hydrochloride (0.4 g) as colorless prisms, m.p. 182°–185° C.

Elemental Analysis for $C_{33}H_{44}N_2O_6.HCl$: Calcd.: C 65.93; H 7.54; N 4.66. Found: C 65.57; H 7.55; N 4.62.

EXAMPLE 24

A mixture of 3-methoxy-2-naphthoic acid (1 g), thionyl chloride (3 ml) and benzene (20 ml) is heated for one hour under reflux. The reaction mixture is concentrated under reduced pressure. to the residue is added toluene (10 ml), and the mixture is again concentrated under reduced pressure. Thus-obtained 3-methoxy-2-naphthoyl chloride is dissolved in toluene (20 ml). The solution is added dropwise to a mixture of 1-(3,4,5-trimethoxybenzyl)piperazine dihydrochloride (1.8 g), triethylamine (2.5 g) and N,N-dimethyl acetamide (20 ml) at room temperature with stirring. Then, the mixture is stirred for one hour. Water (100 ml) ethyl acetate (100 ml) and hexane (50 ml) are added to the mixture, and the mixture is shaken thoroughly. The organic layer is separated, washed with water, dried and concentrated under reduced pressure. Thus-obtained oily product is purified by silica gel column chromatography (hexane:acetone=2:3–1:2) and converted to the hydrochloride in ethyl acetate and diluted with ethyl ether to allow powders to precipitate. The supernatant is removed by decantation, and the precipitates are dried under reduced pressure to yield 1-(3-methoxy-2-napthoyl)-4-(3,4,5-trimethoxybenzyl)piperazine hydrochloride (1.9 g) as colorless powder.

Elemental Analysis for $C_{26}H_{30}N_2O_5.HCl.3/2H_2O$: Calcd.: C 60.75; H 6.67; N 5.45. Found: C 60.92; H 6.17; N 5.44.

Mass Spectrum (m/z): 450 (M+).

EXAMPLE 25

Using 1-methoxy-2-naphthoic acid (1 g) and thionyl chloride (3 ml), a reaction as that described in Example 24 is carried out to give 1-methoxy-2-naphthoyl chloride, which is allowed to react with 1-(3,4,5-trimethoxybenzyl)piperazine dihydrochloride (1.8 g). The product is purified by silica gel column chromatography (hexane:acetone=3:2–1:2) and then converted to the hydrochloride in a mixture of ethyl acetate and ethyl ether. Thus-obtained powder is recrystallized from ethyl acetate to afford 1-(1-methoxy-2-naphthoyl)-4-(3,4,5-trimethoxybenzyl) piperazine hydrochloride (1.7 g) as colorless crystals, m.p. 194°–197° C. (decomp.).

Elemental Analysis for $C_{26}H_{30}N_2O_5.HCl.H_2O$: Calcd.: C 61.84; H 6.59; N 5.55. Found: C 61.91; H 6.35; N 5.30.

EXAMPLE 26

Anthraquinone-2-carboxylic acid (1 g) is allowed to react, in a manner as that described in Example 24, with thionyl chloride (3 ml). Then the acid chloride thus obtained is allowed to react with 1-(3,4,5-trimethoxybenzyl)piperazine dihydrochloride (1.5 g). The product is crystallized from ethyl acetate-ethyl ether to yield 1-(2-anthraquinonylcarbonyl)-4-(3,4,5-trimethoxybenzyl)piperazine (0.7 g) as pale yellow crystals, m.p. 158°–160° C.

Elemental Analysis for $C_{29}H_{28}N_2O_6$: Cacld.: C 69.59; H 5.64; N 5.60. Found: C 69.63; H 5.68; N 5.58.

EXAMPLE 27

A mixture of powdery sodium methoxide prepared by subjecting a 28% methanol solution of sodium methoxide (14 g) to concentration under reduced pressure, 6,7-dibenzyloxy-3,4-dihydro-1 (2H)-naphthalenjone (7.17 g) and dimethyl carbonate (36 g) is heated under reflux for 5 hours in a stream of nitrogen. To the reaction mixture are added water (100 ml), ethyl acetate (200 ml) and hexane (50 ml). The mixture is then made acid with hydrochloric acid and shaken thoroughly. The organic layer is separated, washed with water, dried and concentrated under reduced pressure to give 6,7-dibenzyloxy-1-oxo-1,2,3,4-tetrahydro-2-naphthoic acid methyl ester. This product is dissolved in a mixture of methanol (100 ml) and methylene chloride (100 ml). Sodium borohydride (0.5 g) is added to the solution with stirring at room temperature. After stirring for 30 minutes, further sodium borohydride (0.5 g) is added to the mixture and stirred for 30 minutes, followed by addition of water (500 ml). The methylene chloride layer is separated, and the aqueous layer is extracted with methylene chloride (100 ml). The organic layers are combined and concentrated under reduced pressure. The residue is purified by silica gel column chromatography (hexane:ethyl acetate=4:1–2:1) to give a colorless oily product. This product is crystallized from ethyl ether to give 6,7-dibenzyloxy-1-hydroxy-1,2,3,4-tetrahydro-2-naphthoic acid methyl ester (2.6 g) as colorless crystals, m.p. 121°–124° C.

Elemental Analysis for $C_{26}H_{26}O_5$: Calcd.: C 74.62; H 6.26. Found: C 74.89; H 6.32.

This product (2.5 g) is dissolved in methanol (100 ml). An aqueous solution (10 ml) of sodium hydroxide (3 g) is added dropwise to the solution, and the mixture is left standing for one hour. Insolubles are filtered off, and the filtrate is concentrated under reduced pressure. to the concentrate is added water (200 ml), and the mixture is made acid with hydrochloric acid and then extracted with ethyl acetate. The organic layer is washed with water, dried and concentrated under reduced pressure. Dioxane (10 ml) and concentrated hydrochloride acid (4 ml) is added to the residue, and the mixture is kept at 80° C. for 2 minutes, then at room temperature for 30 minutes. To the reaction mixture is added water (200 ml), and then the resulting precipitates are collected by filtration and recrystallized from a mixture of acetone and ethanol to yield 6,7-dibenzyloxy-1,2-dihydro-3-naphthoic acid (1.7 g) as colorless prisms, m.p. 173°–176° C.

Elemental Analysis for $C_{25}H_{22}O_4$: Calcd.: C 77.70; H 5.74. Found: C 77.53; H 5.75.

EXAMPLE 28

Using 6,7-dibenzyloxy-1,2-dihydro-3-naphthoic acid (0.5 g), 1-(3,4,5-trimethoxybenzyl)piperazine dihydrochloride (0.69 g), triethylamine (0.52 g), N,N-dimethylformamide (10 ml) and diethyl phosphorocyanidate (0.75 ml), as amidation as that described in Example 6 is carried out. The product is purified by silica gel column chromatography (hexane:acetone=1:1–1:2) and converted to the hydrochloride in a mixture of ethyl acetate and ethyl ether to yield 1-(6,7-dibenzyloxy-1,2-dihydro-3-naphthoyl)-4-(3,4,5-trimethoxybenzyl)piperazine hydrochloride (0.6 g) as colorless crystals, m.p. 186°–190° C.

Elemental Analysis for $C_{39}H_{42}N_2O_6 \cdot HCl$: Calcd.: C 69.79; H 6.46; N 4.17. Found: C 70.01; H 6.47; N 4.14.

EXAMPLE 29

Using powdery sodium methoxide [prepared by subjecting a 28% methanol solution of sodium methoxide (14 g) to concentration to dryness under reduced pressure], 6-benzyloxy-3,4-dihydro-1(2H)-naphthalenone (5.1 g) and dimethyl carbonate (36 g), a condensation reaction is carried out in a manner as that described in Example 27, followed by conducting reduction with sodium borohydride (1 g). The product is purified by silica gel column chromatography (hexane:ethyl acetate=4:1–2:1), followed by recrystallization from ethyl ether to obtain methyl ester of 6-benzyloxy-1-hydroxy-1,2,3,4-tetrahydro-2-naphthoic acid (2.5 g) as colorless crystals, m.p. 123°–127° C.

Elemental Analysis for $C_{19}H_{20}O_4$: Calcd.: C 73.06; H 6.45. Found: C 73.25; H 6.48.

EXAMPLE 30

An aqueous solution (10 ml) of sodium hydroxide (3 g) is added to a solution of methyl ester of 6-benzyloxy-1-hydroxy-1,2,3,4-tetrahydro-2-naphthoic acid (1 g) dissolved in methanol (80 ml) and the mixture is left standing. After 30 minutes, the mixture is concentrated under reduced pressure. Water (50 ml) is added to the mixture, and then precipitating crystals are collected by filtration. The crystals are washed with water and acetone. The crystals (0.9 g) is added to a mixture of methanol (75 ml), water (25 ml) and 10% palladium carbon (50% water-content) (1 g). The mixture is catalytically hydrogenated at room temperature under atomospheric pressure of hydrogen gas. After hydrogen absorption has ceased, the catalyst is filtered off, and the filtrate is concentrated under reduced pressure. To the residue are added dioxane (30 ml), concentrated hydrochloric acid (2 ml) and water (10 ml), and the mixture is left standing at room temperature for one hour. The resultant is concentrated under reduced pressure. The precipitating crystals are treated with water (10 ml) and collected by filtration to give 7-hydroxy-1,2-dihydro-3-naphthoic acid (0.4 g) as colorless prisms, m.p. 195°–197° C.

Elemental Analysis for $C_{11}H_{10}O_3 \cdot \frac{1}{2}H_2O$: Calcd.: C 66.32; H 5.57. Found: C 66.39; H 5.96.

EXAMPLE 31

Methyl ester of 6-benzyloxy-1-hydroxy-1,2,3,4-tetrahydro-2-naphthoic acid (0.6 g) is dissolved in methanol (50 ml). To the solution is added an aqueous solution (10 ml) of sodium hydroxide (2 g), and the mixture is left standing for 30 minutes at room temperature. The resultant is concentrated under reduced pressure. The concentrate is diluted with water (50 ml). The precipitating crystals are collected by filtration. This product is dissolved in a mixture of dioxane (50 ml) and concentrated hydrochloric acid (2 ml). The mixture is left standing for 5 minutes at 80° C. and then for 30 minutes at room temperature. The resultant is concentrated under reduced pressure. Water (50 ml) is added to the concentrate. The precipitating crystals are collected by filtration to give 7-benzyloxy-1,2-dihydro-3-naphthoic acid (0.45 g) as colorless crystals, followed by recrystallization from a mixture of methanol and acetone to afford colorless needles, m.p. 202°–205° C.

Elemental Analysis for $C_{18}H_{16}O_3$: Calcd.: C 77.12; H 5.75. Found: C 76.96; H 5.73.

EXAMPLE 32

Using 7-benzyloxy-1,2-dihydro-3-naphthoic acid (0.4 g), 1-(3,4,5-trimethoxybenzyl)piperazine dihydrochloride (0.76 g), triethylamine (0.6 g), N,N-dimethylformamide (10 ml) and diethyl phosphorocyanidate (0.75 ml), an amidation as that described in Example 6 is carried out. The reaction product is purified by silica gel column chromatography (hexane:acetone=1:1–1:2) and converted to the hydrochloride in a mixture of ethyl acetate and ethyl ether to yield 1-(7-benzyloxy-1,2-dihydro-3-naphthoyl)-4-(3,4,5-trimethoxybenzyl)piperazine hydrochloride (0.6 g) as colorless crystals, m.p. 196°–199° C. (decomp.).

Elemental Analysis for $C_{32}H_{36}N_2O_5 \cdot HCl$: Calcd.: C 68.01; H 6.60; N 4.96. Found: C 67.73; H 6.57; N 4.90.

EXAMPLE 33

Dicyclohexylcarbodiimide (0.48 g) is added to a mixture of 7-hydroxy-1,2-dihydro-3-naphthoic acid (0.4 g), N-hydroxy-5-norbornene-2,3-dicarboxyimide (0.45 g), dioxane (5 ml) and tetrahydrofuran (5 ml) under ice-cooling, and the mixture is stirred for 15 minutes, then left standing for one hour at room temperature. The reaction mixture is concentrated to about half of its original volume. Then insolubles are filtered off. The filtrate is added dropwise to a mixture of 1-(3,4,5-trimethoxybenzyl)piperazine dihydrochloride (0.9 g), triethylamine (0.51 g) and N,N-dimethylforamide (5 ml) with stirring at room temperature. The mixture is left standing overnight and then shaken with a mixture of water (100 ml) and ethyl acetate (100 ml). The organic layer is separated, washed with water, dried and concentrated under reduced pressure. The residue is purified by silica gel column chromatography (hexane:acetone=1:1–1:2) to obtain 1-(7-hydroxy-1,2-dihydro-3-naphtholyl)-4-(3,4,5-trimethoxybenzyl)piperazine (0.45 g) as a colorless oil. This product (0.25 g) is converted to the hydrochloride in a mixture of ethyl acetate and ethanol to give colorless crystals (0.22 g), m.p. 137°–142° C. (decomp.).

Elemental Analysis for $C_{25}H_{30}N_2O_5 \cdot HCl \cdot H_2O$: Calcd.: C 60.91; H 6.75; N 5.68. Found: C 61.41; H 6.49; N 5.55.

EXAMPLE 34

1-(6,7-dibenzyloxy-1,2-dihydro-3-naphthoyl)-4-(3,4,5-trimethoxybenzyl)piperazine hydrochloride (0.4 g) is dissolved in acetic acid (8 ml). To the solution is added a 30% solution of hydrogen bromide-acetic acid (4 ml), and the mixture is left standing at room temperature for one hour. To the reaction mixture is added ethyl ether (200 ml), and the mixture is left standing, and then the supernatant is removed by decantation. The precipitates are washed twice with 50 ml each portion of ethyl ether, followed by addition of ethanol (10 ml), whereupon crystallization occurs. The crystals are diluted in ethyl ether (30 ml). The precipitates are collected by filtration to give 1-(6,7-dihydroxy-1,2-dihydro-3-naphthoyl)-4-(3,4,5-trimethoxybenzyl)piperazine hydrobromide (0.25 g) as colorless crystals, m.p. 258°–262° C.

Elemental Analysis for $C_{25}H_{30}N_2O_6 \cdot HBr \cdot H_2O$: Calcd.: C 54.26; H 6.01; N 5.06. Found: C 53.91; H 5.67; N 4.99.

EXAMPLE 35

A mixture of 1-(7-hydroxy-1,2-dihydro-3-naphthoyl)-4-(3,4,5-trimethoxybenzyl)piperazine (0.2 g), ethyl acetate (20 ml), trimethylamine (0.5 g) and benzoyl chloride (0.5 g) is left standing for 7 hours at room temperature. To the mixture is added ethanol (2 ml), and the mixture is left standing overnight. The solvent is distilled off under reduced pressure. To the residue is added ethyl acetate (50 ml), and insolubles are filtered off. The filtrate is concentrated under reduced pressure. The residue is purified by silica gel column chromatography (hexane:acetone=1:1–1:2) and crystallized from ethyl ether to afford 1-(7-benzoyloxy-1,2-dihydro-3-naphthoyl)-4-(3,4,5-trimethoxybenzyl)piperazine (0.15 g) as colorless prisms, m.p. 117°–119° C.

Elemental Analysis for $C_{32}H_{34}N_2O_6 \cdot \frac{1}{2}H_2O$: Calcd.: C 69.67; H 6.40; N 5.08. Found: C 69.78; H 6.45; N 5.05.

EXAMPLE 36

A mixture of 1-(6,7-dihydroxy-1,2-dihydro-3-naphthoyl)-4-(3,4,5-trimethoxybenzyl)piperazine hydrobromide (0.3 g), ethyl acetate (20 ml), triethylamine (0.5 ml) and acetic anhydride (0.5 ml) is left standing at room temperature overnight. Ethanol (5 ml) is added to the mixture. The whole mixture is left standing for one hour and then concentrated under reduced pressure. The residue is purified by silica gel column chromatography (hexane:acetone=1:1–1:2) to give an oily product. This product is dissolved in ethyl ether. An ethyl ether solution (50 ml) of fumaric acid (0.1 g) is added to the solution. The mixture is diluted with petroleum ether, whereupon colorless powder precipitates out. The precipitates are collected by filtration to give 1-(6,7-diacetyloxy-1,2-dihydro-3-naphthoyl)-4-(3,4,5-trimethoxybenzyl)piperazine fumarate (0.25 g) as colorless powder.

Elemental Analysis for $C_{29}H_{34}N_2O_3 \cdot C_4H_4O_4 \cdot H_2O$: Calcd.: C 58.91; H 5.99; N 4.16. Found: C 58.88; H 5.87; N 3.95.

SIMS spectrum (m/z): 539 (MH+).

EXAMPLE 37

In a manner as that described in Example 5, 2-indane carboxylic acid (0.8 g) is converted to the 2-indane carbonyl chloride by using thionyl chloride (2 ml) in toluene (10 ml). The product thus obtained is added to a mixture of 1-(3,4,5-trimethoxybenzyl)piperazine dihydrochloride (2.1 g), triethylamine (5.9 g) and N,N-dimethylformamide (20 ml). The whole mixture is left standing at room temperature for two hours. A mixture of water (300 ml) and ethyl acetate (300 ml) is added to the mixture, and the mixture is shaken thoroughly. The organic layer is separated, washed with water, dried and concentrated under reduced pressure. The residue is purified by silica gel column chromatography (hexane:acetone=1:1) to give an oily product, which is converted to the hydrochloride in a mixture of methanol and ethyl acetate to give 1-(2-indanylcarbonyl)-4-(3,4,5-trimethoxybenzyl)-piperazine hydrochloride (1.1 g) as colorless crystals, m.p. 227°–232° C. (decomp.).

Elemental Analysis for $C_{24}H_{30}N_2O_4 \cdot HCl \cdot \frac{1}{2}H_2O$: Calcd.: C 63.22; H 7.07; N 6.14. Found: C 62.76; H 7.42; N 5.90.

EXAMPLE 38

A mixture of 9-oxo-2-fluorene carboxylic acid (1 g), toluene (10 ml), and thionyl chloride (3 ml) is heated for one hour under reflux. The mixture is evaporated to dryness. To the residue is added toluene (10 ml), and the mixture is again evaporated to dryness. Thus-obtained yellow powder is mixed with toluene (50 ml), and the mixture is added to a mixture of 1-(3,4,5-trimethoxybenzyl)piperazine dihydrochloride (1.8 g), triethylamine (4.3 g) and N,N-dimethylformamide (20 ml). The resulting mixture is left standing at room temperature for 30 minutes and treated with water (300 ml). The whole mixture is extracted with ethyl acetate (500 ml). The organic layer is washed with water, dried and concentrated to afford 1-(9-oxo-2-fluorenylcarbonyl)-4-(3,4,5-trimethoxybenzyl)piperazine (1.1 g) as pale yellow crystals, m.p. 166°–168° C.

Elemental Analysis for $C_{28}H_{28}N_2O_5$: Calcd.: C 71.17; H 5.97; N 5.93. Found: C 71.11; H 5.97; N 5.78.

EXAMPLE 39

To a mixture of 1-(9-oxo-2-fluorenylcarbonyl)-4-(3,4,5-trimethoxybenzyl)piperazine (0.5 g) and methanol (50 ml) is added sodium borohydride (0.2 g). The mixture is stirred for 30 minutes. The solvent is distilled off under reduced pressure. After addition of water (100 ml), the mixture is extracted with methylene chloride (100 ml). The organic layer is dried and evaporated to dryness under reduced pressure. The residue is dissolved in a mixture of ethanol and ethyl ether. The solution is treated with a 1N hydrogen chloride-ethyl acetate solution (2 ml), and the resulting precipitates are collected by filtration to thereby give 1-(9-hydroxy-2-fluorenylcarbonyl)-4-(3,4,5-trimethoxybenzyl)piperazine hydrochloride (0.5 g) as colorless powder.

Elemental Analysis for $C_{28}H_{30}N_2O_5 \cdot HCl \cdot 3/2H_2O$: Calcd.: C 62.51; H 6.37; N 5.21. Found: C 62.83; H 5.99; N 5.20.

EXAMPLE 40

A mixture of 6,7-dimethoxy-1-oxo-1,2,3,4-tetrahydro-2-naphthoic acid methyl ester (1.5 g) and powdery sulfur (0.5 g) is heated at 200–210° C. for 2 hours. The reaction mixture is, after cooling, purified by silica gel column chromatography (hexane:ethyl acetate=2:1), followed by crystallization from a mixture of ethyl ether and petroleum ether to afford 6,7-dimethoxy-1-hydroxy-2-napthoic acid methyl ester (0.3 g) as colorless needles, m.p. 144°–145° C.

Elemental Analysis for $C_{14}H_{14}O_5$: Calcd.: C 64.12; H 5.38. Found: C 64.19; H 5.41.

This product (0.5 g) is dissolved in acetone (20 ml), to which is added an aqueous solution (200 ml) of sodium hydroxide (5 g). The mixture is left standing at room temperature for two days. The reaction mixture is made acid with hydrochloric acid. Then precipitating solid matter is collected by filtration and dissolved in acetone (100 ml), and then the insolubles are filtered off. The filtrate is concentrated under reduced pressure. Ethanol (5 ml) is added to the residue. Then precipitating crystals are collected by filtration to give 6,7-dimethoxy-1-hydroxy-2-naphthoic acid (0.28 g), m.p. 205°–208° C. (decomp.).

Elemental Analysis for $C_{13}H_{12}O_5$: Calcd.: C 62.90; H 4.87. Found: C 62.98; H 4.93.

EXAMPLE 41

Dicyclohexylcarbodiimide (0.31 g) is added to an ice-cooling mixture of 6,7-dimethoxy-1-hydroxy-2-naphthoic acid (0.25 g), tetrahydrofuran (2 ml), dioxane (2 ml), N,N-dimethylformamide (1 ml) and N-hydroxy-5-norbornene-2,3-dicarboxyimide (0.25 g). The mixture is left standing at room temperature for 30 minutes and filtered off. The filtrate is added to a mixture of 1-(3,4,5-trimethoxybenzyl)piperazine dihydrochloride (0.43 g), triethylamine (0.24 g) and N,N-dimethylformamide (4 ml). The whole mixture is left standing at room temperature overnight, and then extracted with a mixture of water (200 ml) and ethyl acetate (200 ml). The organic layer is washed with water, dried and evaporated under reduced pressure. The residue is purified by silica gel column chromatography (hexane:acetone=1:1). The oily product thus-obtained is converted to the hydrochloride in ethyl acetate to yield 1-(6,7-dimethoxy-1-hydroxy-2-naphthoyl)-4-(3,4,5-trimethoxybenzyl)piperazine hydrochloride (0.35 g) as colorless crystals, m.p. 220°–225° C. (decomp.).

Elemental Analysis for $C_{27}H_{32}N_2O_7\cdot HCl$: Calcd.: C 60.84; H 6.24; N 5.26. Found: C 60.56; H 6.28; N 5.11.

SIMS spectrum (m/z): 497 ($MH^+$)

EXAMPLE 42

A mixture of 1,2-dimethoxy-6,7,8,9-tetrahydro-5H-benzocyclohepten-5-one [Itoh et al., Chem. Pharm. Bull., 26, 504 (1978)] (2.2 g), powdery sodium methoxide [prepared by subjecting a 28% methanol solution of sodium methyoxide (8.5 g) to evaporation to dryness under reduced pressure] and dimethyl carbonate (40 ml) is heated for 9 hours under reflux in a stream of nitrogen. After cooling and subsequent addition of water (100 ml) and ethyl acetate (200 ml), the mixture is made acid with hydrochloric acid and shaken thoroughly. The organic layer is separated and evaporated under reduced pressure to give methyl ester of 1,2-dimethoxy-5-oxo-6,7,8,9,-tetrahydro-5H-benzocycloheptene-6-carboxylic acid. This product is dissolved in a mixture of methylene chloride (50 ml) and methanol (50 ml). To the solution is added sodium borohydride (0.5 g), and the mixture is stirred for 30 minutes. After addition of water (200 ml), the reaction mixture is extracted with methylene chloride (100 ml). The organic layer is evaporated under reduced pressure. The residue is purified by silica gel column chromatography (hexane:ethyl acetate=2:1) to give methyl ester of 1,2-dimethoxy-5-hydroxy-6,7,8,9-tetrahydro-5H-benzocycloheptene-6-carboxylic acid (1.6 g) as a pale yellow oily product.

Mass spectrum (m/z): 280 ($M^+$)

This product (1.6 g) is dissolved in methanol (20 ml). An aqueous solution (10 ml) of sodium hydroxide (5 g) is added dropwise to the solution. The mixture is left standing for one hour at room temperature, and then diluted with water (50 ml) and extracted with ethyl ether. The aqueous layer is made acid with dilute hydrochloric acid and extracted with ethyl acetate. The extract solution is washed with water, dried and evaporated under reduced pressure. To the residue are added dioxane (30 ml) and concentrated hydrochloric acid (6 ml). The mixture is heated at 70° C. for one hour, and then concentrated under reduced pressure.

The concentrate is diluted with water (50 ml), and left standing at room temperature. The resulting precipitates are collected by filtration to give 3,4-dimethoxy-6,7-dihydro-5H-benzocycloheptene-8-carboxylic acid (1.1 g) as colorless needles, m.p. 208°–209° C.

Elemental Analysis for $C_{14}H_{16}O_4$: Calcd.: C 67.73; H 6.50. Found: C 67.82; H 6.49.

EXAMPLE 43

Using a mixture of 3,4-dimethoxy6,7-dihydro-5H-benzocycloheptene-8-carboxylic acid (0.6 g), 1-(3,4,5-trimethoxybenzyl)piperazine dihydrochloride (1.3 g), triethylamine (1.5 g), N,N-dimethylformamide (20 ml) and diethyl phosphorocyanidate (0.6 ml), an amidation as that described in Example 6 is carried out. The product is purified by silica gel column chromatography (hexane:acetone=1:1), and converted to the hydrochloride in a mixture of ethyl acetate and ethyl ether to yield 1-(3,4-dimethoxy-6,7-dihydro-5H-benzocyclohepten-8-ylcarbonyl)-4-(3,4,5-trimethoxybenzyl)piperazine hydrochloride (0.55 g) as colorless crystals, m.p. 225°–229° C. (decomp.).

Elemental Analysis for $C_{28}H_{36}N_2O_6\cdot HCl$: Calcd.: C 63.09; H 7.00; N 5.26. Found: C 62.71; H 7.07; N 5.15.

EXAMPLE 44

Using 1-oxo-1,2,3,4-tetrahydro-6-naphthoic acid [Itoh et al., Chem. Pharm. Bull., 32, 130 (1984)] (0.8 g), 1-(3,4,5-trimethoxybenzyl)piperazine dihydrochloride (2.25 g), triethylamine (1.7 g), N,N-dimethylformamide (10 ml) and diethyl phosphorocyanidate (1.6 ml), an amidation as that described in Example 6 is carried out. The product is purified by silica gel column chromatography (hexane:acetone=1:1), and converted to the hydrochloride in a mixture of ethanol, ethyl acetate and ethyl ether to give 1-(1-oxo-1,2,3,4-tetrahydro-6-naphthoyl)-4-(3,4,5-trimethoxybenzyl)piperazine hydrochloride (1.5 g) as colorless crystals, m.p. 210°–215° C. (decomp.).

Elemental Analysis for $C_{25}H_{30}N_2O_5\cdot HCl$: Calcd.: C 63.22; H 6.58; N 5.90. Found: C 62.87; H 6.57; N 5.85.

EXAMPLE 45

To a mixture of 1-(1-oxo-1,2,3,4-tetrahydro-6-naphthoyl)-4-(3,4,5-trimethoxybenzyl)piperazine hydrochloride (0.5 g) and methanol (10 ml) is added sodium borohydride (0.3 g), and the whole mixture is stirred at room temperature for 30 minutes. After addition of water (100 ml), the mixture is extracted with methylene chloride (100 ml). The extract solution is washed with water, dried and evaporated under reduced pressure. The residue is dissolved in a mixture of ethanol (5 ml) and fumaric acid (0.1 g). To the solution are added ethyl ether (100 ml) and petroleum ether (100 ml), and the mixture is left standing overnight. The resulting precipitates are collected by filtration to give 1-(1-hydroxy-1,2,3,4-tetrahydro-6-naphthoyl)-4-(3,4,5-trimethoxybenzyl)piperazine fumarate (0.4 g) as colorless powder.

Elemental Analysis for $C_{25}H_{32}N_2O_5\cdot C_4H_4O_4$: Calcd.: C 62.58; H 6.52; N 5.03. Found: C 62.55; H 6.71; N 5.09.

EXAMPLE 46

A mixture of 7-hydroxy-1,2-dihydro-3-naphthoic acid (1 g), potassium carbonate (5 g), potassium iodide (2.5 g), N,N-dimethylformamide (30 ml) and methoxy ethyl bromide (2 ml) is stirred for 12 hours at 100° C. After cooling, water (300 ml) and ethyl acetate (200 ml) are added to the reaction mixture, and the mixture is shaken thoroughly. The organic layer is separated, washed with water, dried and evaporated under reduced pressure. the residue is purified by silica gel column chromatography (hexane:ethyl acetate=4:1-2:1) to give a colorless oily product, which is dissolved in methanol (50 ml). To the solution is added an aqueous solution (10 ml) of sodium hydroxide (2 g). The mixture is left standing for one hour, and then acidified with hydrochloric acid, followed by addition of water (300 ml). The resulting precipitates are collected by filtration and recrystallized from a mixture of methanol and water to give 7-methoxyethoxy-1,2-dihydro-3-naphthoic acid (0.65 g) as colorless needles, m.p. 122°–127° C.

Elemental Analysis for $C_{14}H_{16}O_4$: Calcd.: C 67.73; H 6.50. Found: C 67.46; H 6.43.

EXAMPLE 47

Using 7-methoxy-1,2-dihydro-3-naphthoic acid (0.5 g), 1-(3,4,5-trimethoxybenzyl)piperazine dihydrochloride (1.1 g), triethylamine (0.81 g), N,N-dimethylformamide (20 ml) and diethyl phosphorocyanidate (1 ml), an amidation is carried out in a manner as that described in Example 6. The reaction product is purified by silica gel column chromatography (hexane:acetone=1:1-1:2) to afford an oily product, which is converted to the hydrochloride in ethyl acetate to give 1-(7-methoxyethoxy-1,2-dihydro-3-naphthoyl)- 4-(3,4,5-trimethoxybenzyl)piperazine hydrochloride (0.8 g) as colorless crystals, m.p. 187°–190° C.

Elemental Analysis for $C_{28}H_{36}N_2O_6.HCl$: Calcd.: C 63.09; H 7.00; N 5.26. Found: C 63.09; H 6.97; N 5.26.

EXAMPLE 48

Using 2,3-dimethoxy-6,7,8,9-tetrahydro-5H-benzocyclohepten-5-one (10 g), powdery sodium methoxide [prepared by subjecting a 28% methanol solution of sodium methoxide (40 g) to concentration to dryness under reduced pressure] and dimethyl carbonate (150 g), a condensation reaction is carried out in a manner as that described in Example 42. The resulting methyl ester of 2,3-dimethoxy-5-oxo-6,7,8,9-tetrahydro-5H-benzocycloheptene-6-carboxylic acid is dissolved in a mixture of methanol (100 ml) and methylene chloride (100 ml). The solution is subjected to reduction in a manner as that described in Example 42, using sodium borohydride (2 g). The product is purified by silica gel column chromatography (hexane:ethyl acetate=2:1-1:1) to afford 2,3-dimethoxy-5-hydroxy-6,7,8,9-tetrahydro-5H-benzocycloheptene-6-carboxylic acid methyl ester (8 g) as a pale yellow oil.

IR spectrum $\nu_{max}^{neat}$ cm$^{-1}$: 3500 (OH), 1720 (C=O).

This product (8 g) is dissolved in methanol (20 ml). An aqueous solution (100 ml) of sodium hydroxide (16 g) is added dropwise to the solution. The mixture is stirred for 30 minutes. After addition of water (100 ml), the mixture is extracted with ethyl ether. The aqueous layer is acidified with hydrochloric acid and extracted with ethyl acetate. The extract solution is washed with water, dried and evaporated under reduced pressure. To the residue are added dioxane (50 ml), concentrated hydrochloric acid (5 ml) and water (10 ml), and the mixture is heated at 70° C. for one hour. The reaction mixture is concentrated under reduced pressure. The concentrate is diluted with water (50 ml). The resulting precipitates are collected by filtration to give 2,3-dimethoxy-6,7-dihydro-5H-benzocycloheptene-8-carboxylic acid (5.5 g) as colorless needles, m.p. 158°–159° C.

Elemental Analysis for $C_{14}H_{16}O_4$: Calcd.: C 67.73; H 6.50. Found: C 67.97; H 6.55.

EXAMPLE 49

Using 2,3-dimethoxy-6,7-dihydro-5H-benzocycloheptene-8-carboxylic acid (2 g), 1-(3,4,5-trimethoxybenzyl)piperazine dihydrochloride (3.5 g), N,N-dimethylformamide (30 ml), triethylamine (3.3 g) and diethyl phosphorocyanidate (2.5 ml), a reaction as that described in Example 6 is carried out. The product is purified by silica gel column chromatography (hexane:acetone=1:1) to give an oily product which is converted to the hydrochloride in ethyl acetate to yield 1-(2,3-dimethoxy-6,7-dihydro-5H-benzocyclohepten-8-ylcarbonyl)-4-(3,4,5-trimethoxybenzyl)piperazine hydrochloride (1.2 g) as colorless crystals, m.p. 138°–142° C.

Elemental Analysis for $C_{28}H_{36}N_2O_6.HCl.2H_2O$: Calcd.: C 59.10; H 7.26; N 4.92. Found: C 59.02; H 6.76; N 4.90.

EXAMPLE 50

To a mixture of 1-(2,3-dimethoxy-6,7-dihydro-5H-benzocyclohepten-8-ylcarbonyl)piperazine (0.4 g), 3,4,5-trimethoxybenzaldehyde (0.5 g) and ethanol (15 ml) is added sodium cyanoborohydride (0.1 g) in limited amounts with stirring. After stirring for three hours, sodium cyanoborohydride (0.1 g) is added to the reaction mixture, and the mixture is stirred for three hours. The reaction mixture is poured into ice-water (100 ml), and extracted with ethyl acetate. The organic layer is washed with water, dried and concentrated under reduced pressure. The residue is purified by silica gel column chromatography (hexane:acetone=1:1). Thus-obtained oily product is converted to its hydrochloride in ethyl acetate to thereby obtain 1-(2,3-dimethoxy-6,7-dihydro-5H-benzocyclohepten-8-ylcarbonyl)-4-(3,4,5-trimethoxybenzyl)piperazine hydrochloride (0.4 g), as obtained in Example 49, as colorless crystals, m.p. 138°–142° C.

EXAMPLE 51

A mixture of 1-(2,3-dimethoxy-6,7-dihydro-5H-benzocyclohepten-8-ylcarbonyl)piperazine (0.4 g), 3,4,5-trimethoxybenzyl chloride (0.3 g), anhydrous potassium carbonate (0.3 g) and acetonitrile (15 ml) is heated for five hours under reflux. The reaction mixture is subjected to filtration, and the filtrate is concentrated under reduced pressure. The concentrate is purified by silica gel column chromatography (hexane:acetone=1:1). Thus-obtained oily product is led to its hydrochloride in ethyl acetate to thereby obtain 1-(2,3-dimethoxy-6,7-dihydro-5H-benzocyclohepten-8-ylcarbonyl)-4-(3,4,5-trimethoxybenzyl)piperazine hydrochloride (0.47 g), as obtained in Example 49, as colorless crystals, m.p. 138°–142° C.

EXAMPLE 52

To a mixture of 3,4,5-trimethoxybenzyl alcohol (2.0 g), triethylamine (1.5 g) and methylene chloride (20 ml) is added dropwise methanesulfonyl chloride (1.3 g) with stirring under ice-cooling. After stirring for three hours, the reaction mixture is poured into ice-water, which is extracted with methylene chloride. The organic layer is washed with an aqueous solution of sodium hydrogencarbonate, which is dried and then concentrated under reduced pressure. The concentrate is dissolved in acetonitrile (30 ml), and to the solution are added 1-(2,3-dimethoxy-6,7-dihydro-5H-benzocyclohepten-8-ylcarbonyl)piperazine (3.0 g) and anhydrous potassium carbonate (2.3 g). The reaction mixture is heated for three hours under reflux. After cooling, the reaction mixture is subjected to filtration, and the filtrate is concentrated under reduced pressure. The concentrate is purified by silica gel column chromatography (hexane:acetone=1:1). The oily product thus-obtained is led to its hydrochloride to obtain 1-(2,3-dimethoxy-6,7-dihydro-5H-benzocyclohepten-8-ylcarbonyl)-4-(3,4,5-trimethoxybenzyl)piperazine hydrochloride (2.9 g), as obtained in Example 49, as colorless crystals, m.p. 138°–142° C.

EXAMPLE 53

A mixture of 3,4,5-trimethoxybenzyl chloride (10.5 g), N-formyl homopiperazine (6.82 g), potassium carbonate (8 g) and ethyl acetate (40 ml) is heated at 50–60° C. for 4 hours. After addition of water the reaction mixture is shaken thoroughly. The organic layer is separated, washed with water, dried and evaporated under reduced pressure. To the residue is added 10% hydrochloric acid (20 ml), and the mixture is extracted with ethyl acetate. The aqueous layer is made alkaline (>pH 9) with a 20% aqueous solution of sodium hydroxide, and extracted with methylene chloride. The extract solution is evaporated under reduced pressure. To the residue is added 10% hydrochloric acid (15 ml), and the mixture is stirred at 100° C. for 3 hours. The reaction mixture is made alkaline with a 20% aqueous solution of sodium hydroxide, and extracted with ethyl acetate. The extract solution is dried and evaporated under reduced pressure. The residue is converted to the hydrochloride in a mixture of ethyl acetate and ethanol to yield 1-(3,4,5-trimethoxybenzyl) homopiperazine dihydrochloride (2.7 g) as colorless powdery crystals, m.p. 216°–220° C.

Elemental Analysis for $C_{15}H_{24}N_2O_3\cdot 2HCl$: Calcd.: C 51.00; H 7.42; N 7.93. Found: C 50.51; H 7.42; N 7.77.

EXAMPLE 54

Using 6,7-dimethoxy-1,2-dihydro-3-naphthoic acid (0.8 g), toluene (8 ml) and thionyl chloride (2 ml), a reaction as that described in Example 5 is carried out to give 6,7-dimethoxy-1,2-dihydro-3-naphthoyl chloride. This product is dissolved in N,N-dimethylformamide (3 ml). The solution is added dropwise to a mixture of 1-(3,4,5-trimethoxybenzyl) homopiperazine dihydrochloride (1.2 g), triethylamine (1.36 g) and N,N-dimethylformamide (5 ml) with stirring under ice-cooling. The resulting mixture is stirred at room temperature for two hours. After addition of water, the reaction mixture is extracted with ethyl acetate. The ethyl acetate layer is washed with water, dried and evaporated under reduced pressure. The residue is purified by silica gel column chromatography (ethyl acetate: methylene chloride:ethanol=10:10:1). The resulting oily product is converted to the hydrochloride in ethyl ether to afford 1-(6,7-dimethoxy-1,2-dihydro-3-naphthoyl)-4-(3,4,5-trimethoxybenzyl)homopiperazine hydrochloride (1.4 g) as pale yellow powder.

Elemental Analysis for $C_{28}H_{36}N_2O_6\cdot HCl\cdot 3/2H_2O$: Calcd.: C 60.05; H 7.20; N 5.00. Found: C 59.69; H 6.97; N 4.85.

IR $\nu_{max}^{KBr}$ cm$^{-1}$: 1610 (C=O).

EXAMPLE 55

A mixture of 3,4,5-trimethoxy benzoic aicd (3 g), thionyl chloride (5 ml) and toluene (20 ml) is heated for one hour under reflux, followed by evaporation to dryness under reduced pressure. The residue is dissolved in N,N-dimethylformamide (5 ml). The solution is added dropwise to a mixture of N-formylpiperazine (1.61 g), triethylamine (2.9 ml) and N,N-dimethylformamide (10 ml) with stirring under ice-cooling. The resulting mixture is stirred for 30 minutes at room temperature. After addition of water, the reaction mixture is made alkaline with a 1N aqueous solution of sodium hydroxide and then extracted with methylene chloride. The extract solution is evaporated under reduced pressure. To the residue are then added methanol (10 ml) and 10% hydrochloric acid (15 ml), and the mixture is stirred at 100° C. for two hours. The reaction mixture is evaporated under reduced pressure. To the residue is added a 1N aqueous solution of sodium hydroxide, and the mixture is extracted with methylene chloride. The extract solution is evaporated under reduced pressure. The residue is dissolved in ethanol (20 ml) and treated with a 5N hydrogen chloride-methanol solution to yield 1-(3,4,5-trimethoxybenzoyl)piperazine hydrochloride (1.8 g) as colorless prisms, m.p. 232°–235° C.

Elemental Analysis for $C_{14}H_{20}N_2O_4\cdot HCl$: Calcd.: C 53.08; H 6.68; N 8.84. Found: C 53.05; H 6.73; N 8.75.

EXAMPLE 56

A mixture of 6,7-dimethoxy-1,2-dihydro-3-naphthoic acid (0.6 g), thionyl chloride (1.5 ml) and toluene (8 ml) is heated for one hour under reflux. The reaction mixture is evaporated under reduced pressure. Toluene (10 ml) is added to the residue, and the mixture is again evaporated under reduced pressure. The resulting 6,7-dimethoxy-1,2-dihydro-3-naphthoyl chloride is dissolved in N,N-dimethylformamide (3 ml). The solution is added, dropwise to a mixture of 1-(3,4,5-trimethoxybenzoyl)piperazine hydrochloride (0.82 g), triethylamine (0.94 g) and N,N-dimethylformamide (6 ml) with stirring under ice-cooling taking 5 minutes. The reaction mixture is stirred at room temperature for one hour. To the reaction mixture is added ice-water (200 ml), and the resulting mixture is extracted with methylene chloride (50 ml×2). The organic layer is concentrated under reduced pressure. The residue is dissolved in ethyl acetate (100 ml), and the solution is washed with water (50 ml×2), then dried over anhydrous sodium sulfate and concentrated under reduced pressure. The residue is purified by silica gel column chromatography(n-hexane:ethyl acetate:acetone:ethanol=10:10:5:1) to afford 1-(6,7-dimethoxy-1,2-dihydro-3-naphthoyl)-4-(3,4,5-trimethoxybenzoyl)piperazine (1.05 g) as crystals. The yield is 83%. Recrystallization of the product from ethyl acetate-hexane gives colorless needles, 160–161° C.

Elemental Analysis for $C_{27}H_{32}N_2O_7$: Calcd.: C 65.31; H 6.50; N 5.64. Found: C 65.60; H 6.53; N 5.64.

NMR spectrum (in $CDCl_3$) δ: 2.4–3.0 (4H, naphthalene ring methylene proton); 3.67 (8H, piperazine ring methylene proton); 3.87 (15H, methoxy proton); 6.56 (1H, vinyl proton); 6.62 (2H, phenyl proton); 6.70 (2H, phenyl proton)

EXAMPLE 57

A mixture of 6,7-dihydroxy-3,4-dihydro-1(2H)-napthalenone [Tamura et al., J. Agr. Chem. Soc. Japan, 27, 318(1953)] (5 g), diethyl sulfate (13 g), potassium carbonate (13.6 g) and acetone (150 ml) is heated for 6 hours under reflux. The reaction mixture is cooled, and insolubles are filtered off. The filtrate is evaporated under reduced pressure. The residue is purified by silica gel column chromatography (hexane:ethyl acetate=3:1) to afford 6,7-diethoxy-3,4-dihydro-1(2H)-naphthalenone (5.9 g), m.p. 77°–78° C. (colorless needles: recrystallized from ethyl acetate-hexane).

Elemental Analysis for $C_{14}H_{18}O_3$: Calcd.: C 71.77; H 7.74. Found: C 71.91; H 7.86.

A mixture of this product (5 g), powdery sodium methoxide [prepared by subjecting a 28% methanol solution of sodium methoxide (22 g) to concentration to dryness under reduced pressure] and dimethyl carbonate (50 ml) is heated under reflux for 5 hours in a stream of nitrogen. After cooling and addition of water the reaction mixture is acidified with dilute hydrochloric acid and extracted with ethyl acetate. The extract solution is washed with water, dried and concentrated under reduced pressure to allow crystals to precipitate. The crystals are collected by filtration to afford 6,7-diethoxy-1-oxo-1,2,3,4-tetrahydro-2-naphthoic acid methyl ester (5.5 g), m.p. 115°–116° C. (colorless needless: recrystallized from ethyl acetate-hexane).

Elemental Analysis for $C_{16}H_{20}O_5$: Calcd.: C 65.74; H 6.90. Found: C 65.74; H 6.93.

This product (5 g) is dissolved in a mixture of methylene chloride (50 ml) and methanol (50 ml). To the solution is added in limited amounts sodium borohydride (0.9 g). To the reaction mixture is added water, and the methylene chloride layer is separated. The aqueous layer is extracted with methylene chloride. The organic layers are combined, washed with water, dried and evaporated under reduced pressure. The resulting 6,7-diethoxy-1-hydroxy-1,2,3,4-tetrahydro-3-naphthoic acid methyl ester is dissolved in methanol (4 ml). To the solution is added dropwise an aqueous solution (25 ml) of sodium hydroxide (5 g), and the mixture is stirred for 30 minutes at room temperature. Water (100 ml) is added to the mixture and the mixture is extracted with ethyl ether. The aqueous layer is acidified with hydrochloric acid and extracted with ethyl acetate. The extract solution is evaporated under reduced pressure. To the residue are added dioxane (40 ml) and concentrated hydrochloric acid (5 ml), and the mixture is heated at 80–90° C. for 15 minutes. The reaction mixture is evaporated under reduced pressure. To the residue is added an aqueous solution (50 ml) of sodium hydroxide (5 g). The mixture is extracted with ethyl ether. The aqueous layer is acidified with hydrochloric acid. Then precipitating crystals are collected by filtration to give 6,7-diethoxy-1,2-dihydro-3-naphthoic acid (3.9 g), m.p. 182°–184° C. (colorless scales: recrystallized from ethyl acetate).

Elemental Analysis for $C_{15}H_{18}O_4$: Calcd.: C 68.69; H 6.92. Found: C 68.81; H 6.99.

EXAMPLE 58

Using 6,7-diethoxy-1,2-dihydro-3-naphthoic acid (1 g), thionyl chloride (2.5 ml) and toluene (10 ml), a reaction as that described in Example 5 is carried out. The resulting 6,7-diethoxy-1,2,-dihydro-3-naphthoyl chloride is dissolved in N,N-dimethylformamide (5 ml). The solution is added dropwise to a mixture of 1-(3,4,5-trimethoxybenzyl) piperazine dihydrochloride (1.36 g), triethylamine (25 ml) and N,N-dimethylformamide (10 ml) under ice-cooling. The resulting mixture is worked up in a manner as that described in Example 5. The resulting product is purified by silica gel column chromatography (hexane:ethyl acetate:acetone=12:8:5) to give 1-(6,7-diethoxy-1,2,-dihydro-3-naphthoyl)-4-(3,4,5-trimethoxybenzyl)-piperazine (1.7 g) as colorless crystals, m.p. 133°–134° C. (colorless needles: recrystallized from ethyl acetate-hexane).

Elemental Analysis for $C_{29}H_{38}N_2O_6$: Calcd.: C 68.21; H 7.50; N 5.49. Found: C 68.33; H 7.52; N 5.42.

This product (1 g) is converted to the hydrochloride in a mixture of ethanol and ethyl ether to yield 1-(6,7-diethoxy-1,2-dihydro-3-naphthoyl)-4-(3,4,5-trimethoxybenzyl)piperazine hydrochloride (0.95 g) as colorless needles, m.p. 204°–208° C. (decomp.).

Elemental Analysis for $C_{29}H_{38}N_2O_6 \cdot HCl$: Calcd.: C 63.67; H 7.19; N 5.12. Found: C 63.54; H 7.13; N 5.11.

EXAMPLE 59

A mixture of 6,7-dihydroxy-3,4-dihydro-1(2H)-naphthalenone (5 g), propyl 1-iodide (12 g), potassium carbonate (11.6 g) and N,N-dimethylformamide (20 ml) is stirred for 5 hours at room temperature. The reaction mixture is poured into water and extracted with ethyl acetate. The extract solution is washed with water, dried and subjected to evaporation under reduced pressure. The residue is purified by silica gel column chromatography (hexane:ethyl acetate=7:1) to afford 6,7-dipropoxy-3,4-dihydro-1(2H)naphthalenone (5.7 g), m.p. 63°–64° C. (colorless needles: recrystallized from ethyl ether-hexane).

Elemental Analysis for $C_{16}H_{22}O_3$: Calcd.: C 73.25; H 8.45. Found: C 73.32; H 8.46.

Using this product (5.3 g), powdery sodium methoxide (prepared by subjecting a 28% methanol solution of sodium methoxide to evaporation to dryness under reduced pressure and dimethyl carbonate (50 ml), a condensation reaction is carried out in a manner as that described in Example 57 to give methyl ester of 6,7-dipropoxy-1-oxo-1,2,3,4-tetrahydro-2-naphthoic acid (6.3 g) as colorless crystals, m.p. 116°–117° C. (colorless needles: recrystallized from ethyl acetate-hexane).

Elemental Analysis for $C_{18}H_{24}O_5$: Calcd.: C 67.48; H 7.55 Found: C 67.76; H 7.66

This product (5.8 g) is dissolved in a mixture of methylene chloride (50 ml) and methanol (50 ml). The solution is subjected to reduction by using sodium borohydride (1 g) in a manner as that described in Example 57. The resulting methyl ester of 6,7-dipropoxy-1-hydroxy-1,2,3,4-tetrahydro-2-naphthoic acid is hydrolyzed with an aqueous solution of sodium hydroxide in a manner as that described in Example 57, followed by treatment with hydrochloric acid in dioxane to give 6,7-dipropoxy-1,2-dihydro-3-naphthoic acid (3.5 g) as colorless crystals, m.p. 140°–141° C. (colorless scales: recrystallized from ethyl acetate).

Elemental Analysis for $C_{17}H_{22}O_4$: Calcd.: C 70.32; H 7.64. Found: C 70.50; H 7.67.

Example 60

Using 6,7-dipropoxy-1,2-dihydro-3-naphthoic acid (1 g), thionyl chloride (2,5 ml) and toluene (10 ml), a reaction as that described in Example 5 is carried out. The resulting 6,7-dipropoxy-1,2-dihydro-3-naphthoyl chloride is dissolved in N,N-dimethylformamide (5 ml). The soluiton is added dropwise under ice-cooling to a mixture of 1-(3,4,5-trimethoxybenzyl)piperazine dihydrochloride (1.23 g), triethylamine (2.5 ml) and N,N-dimethylformamide (15 ml). The resulting mixture is worked up in a manner as that described in Example 5. The product is purified by silica gel column chromatography (hexane:ethyl acetate:acetone=12:8:5) to afford 1-(6,7-dipropoxy-1,2-dihydro-3-naphthoyl)-4-(3,4,5-trimethoxybenzyl)-piperazine (1.5 g) as colorless crystals, m.p. 100°–101° C. (colorless needles: recrystallized from ethyl acetate-hexane).

Elemental Analysis for $C_{31}H_{42}N_2O_6$: Calcd.: C 69.12; H 7.86; N 5.20. Found: C 69.31; H 7.81; N 5.23.

This product (1 g) is converted to the hydrochloride in ethanol to thereby afford 1-(6,7-dipropoxy-1,2-dihydro-3-naphthoyl)-4-(3,4,5-trimethoxybenzyl)-piperazine hydrochloride (0.9 g) as colorless needles, m.p. 203°–207° C. (decomp.).

Elemental Analysis for $C_{31}H_{42}N_2O_6.HCl$: Calcd.: C 64.74; H 7.54; N 4.87. Found: C 64.73; H 7.61; N 4.87.

EXAMPLE 61

A mixture of 5.6-dimethoxy-1H-indene-2-carboxylic acid (0.5 g), thionyl chloride (1 ml) and toluene (6 ml) is heated for one hour under reflux. The reaction solution is evaporated under reduced pressure. To the residue is added toluene (5 ml), and the mixture is again evaporated under reduced pressure. The resulting 5,6-dimethoxy-1H-indene-2-carbonyl chloride is dissolved in methylene chloride (8 ml). The solution is added dropwise to a mixture of 1-(3,4,5-trimethoxybenzoyl)piperazine hydrochloride (0.8 g), triethylamine (0.72 g) and methylene chloride (12 ml) over 3 minutes with stirring under ice-cooling. The mixture is then stirred at room temperature for one hour. To the reaction mixture is added water (50 ml), and the methylene chloride layer is separated. The aqueous layer is extracted with methylene chloride (20 ml). These methylene chloride layers are combined and washed with water, dried and evaporated under reduced pressure. The residue is purified by silica gel column chromatography (hexane:ethyl acetate:acetone=2:2:1) to afford 1-(5,6-dimethoxy-1-H-inden-2-ylcarbonyl)-4-(3,4,5-trimethoxybenzoyl)piperazine (1.03 g). This product is recrystallized from ethyl acetate to give colorless plates, m.p. 183°–185° C.

Elemental Analysis for $C_{26}H_{30}N_2O_7$: Calcd.: C 64.71; H 6.26; N 5.81. Found: C 64.77; H 6.31; N 5.76.

EXAMPLE 62

A mixture of 2,3-dimethoxy-6,7-dihydro-5H-benzocycloheptene-8-carboxylic acid (0.6 g), thionyl chloride (1.2 ml) and toluene (10 ml) is heated for one hour under reflux. The reaction solution is subjected to evaporation under reduced pressure. To the residue is added toluene (8 ml), which is again subjected to evaporation under reduced pressure. The resulting 2,3-dimethoxy-6,7-dihydro-5H-benzocycloheptene-8-carbonyl chloride is dissolved in methylene chloride (10 ml). The solution is added dropwise to a mixture of 1-(3,4,5-trimethoxybenzoyl)piperazine hydrochloride (0.84 g), triethylamine (0.94 g) and methylene chloride (15 ml) over two minutes with stirring under ice-cooling. The resulting mixture is then stirred at room temperature for one hour. To the reaction mixture is added water (60 ml), and the methylene layer is separated. The aqueous layer is subjected to extraction with methylene chloride (30 ml). These methylene chloride layers are combined, washed with water, dried and evaporated under reduced pressure. The residue is purified by silica gel column chromatography (ethyl acetate: hexane:acetone=10:5:8) to give 1-(2,3-dimethoxy-6,7-dihydro-5H-benzocyclohepten-8-ylcarbonyl)-4-(3,4,5-trimethoxybenzoyl)piperazine (1.2 g). This product is recrystallized from a mixture of ethyl acetate and n-hexane to afford colorless prisms, m.p. 164°–165° C.

Elemental Analysis for $C_{28}H_{34}N_2O_7$: Calcd.: C 65.87; H 6.71; N 5.49. Found: C 65.87; H 6.75; N 5.44.

EXAMPLE 63

To a mixture of 1-(2,3-dimethoxy-6,7-dihydro-5H-benzocyclohepten-8-ylcarbonyl)piperazine (0.8 g), 3,4,5-trimethoxy benzoic acid (0.55 g), triethylamine (0.4 g) and N,N-dimethylformamide (10 ml) is added dropwise diethyl phosphorocyanidate (0.5 g) with stirring under ice-cooling. The reaction mixture is stirred for one hour at room temperature. To the reaction mixture are added water (60 ml) and ethyl acetate (50 ml), followed by shaking. The organic layer is separated, washed with water, dried and concentrated under reduced pressure. The residue is purified by silica gel column chromatography (eluent, ethyl acetate:hexane:acetone=10:5:8) to afford 1-(2,3-dimethoxy-6,7-dihydro-5H-benzocyclohepten-8-ylcarbonyl)-4-(3,4,5-trimethoxybenzoyl)piperazine (1.1 g). This product is in agreement with the compound obtained by Example 62 in physico-chemical constants.

EXAMPLE 64

To a mixture of 1-(2,3-dimethoxy-6,7-dihydro-5H-benzocyclohepten-8-ylcarbonyl)piperazine (1.2 g), triethylamine (0.5 g) and methylene chloride (20 ml) is added dropwise, with stirring under ice-cooling, a solution of 3,4,5-trimethoxybenzoyl chloride (1.0 g) in methylene chloride (25 ml). The reaction mixture is stirred for one hour at room temperature. The reaction mixture is pourd into ice-water (100 ml), and extracted with methylene chloride. The organic layer is washed with water, dried and concentrated under reduced pressure. The concentrate is crystallized from ethyl acetate-hexane to give 1-(2,3-dimethoxy-6,7-dihydro-5H-benzocyclohepten-8-ylcarbonyl)-4-(3,4,5-trimethoxybenzoyl)piperazine (1.3 g), as obtained in Example 62, as colorless prisms, m.p. 164°–165° C.

EXAMPLE 65

A mixture of 6,7-diethoxy-1,2-dihydro-3-naphthoic acid (0.8 g), thionyl chloride (1.5 ml) and toluene (12 ml) is heated for one hour under reflux, and the reaction mixture is evaporated under reduced pressure. To the residue is added toluene (10 ml), and the mixture is evaporated again under reduced pressure. The resulting 6,7-diethoxy-1,2-dihydro-3-naphthoyl chloride is dissolved in methylene chloride (8 ml). The solution is added dropwise to a mixture of 1-(3,4,5-trimethoxybenzoyl)piperazine hydrochloride (1.06 g), triethylamine (1.1 g) and methylene chloride (15 ml) over 3 minutes with stirring under ice-cooling. The resulting mixture is then stirred for one hour at room temperature. To the reaction mixture is added water (50 ml), and the methylene chloride layer is separated. The aqueous layer is extracted with methylene chloride (20 ml). These methylene chloride layers are combined, washed with water, dried and evaporated under reduced pressure. The residue is purified by silica gel column chromatography (ethyl acetate:acetone:n-hexane=12:8:5) to afford 1-(6,7-diethoxy-1,2-dihydro-3-naphthoyl)-4-(3,4,5-trimethoxybenzoyl)piperazine (1.45 g). This product is recrystallized from a mixture of ethyl acetate and n-hexane to give colorless needles, m.p. 127°–129° C.

Elemental Analysis for $C_{29}H_{36}N_2O_7$: Calcd.: C 66.40; H 6.92; N 5.34. Found: C 66.42; H 6.88; N 5.32.

EXAMPLE 66

A mixture of 6,7-dipropoxy-1,2-dihydro-3-naphthoic acid (0.8 g), thionyl chloride (1.5 ml) and toluene (12 ml) is heated for one hour under reflux. The reaction mixture is evaporated under reduced pressure. To the residue is added toluene (10 ml), and the mixture is again evaporated under reduced pressure. The resulting 6,7-dipropoxy-1,2-dihydro-3-naphthoyl chloride is dissolved in methylene chloride (8 ml). The solution is added dropwise to a mixture of 1-(3,4,5-trimethoxybenzoyl)piperazine hydrochloride (0.96 g), triethylamine (1.1 g) and methylene chloride (15 ml) over 3 minutes with stirring under ice-cooling. The resulting mixture is then stirred at room temperature for one hour. To the reaction mixture is added water (50 ml), and the methylene chloride layer is separated. The aqueous layer is extracted with methylene chloride. These methylene chloride layers are combined, washed with water, dried and evaporated under reduced pressure. The residue is purified by silica gel column chromatography (ethyl acetate:n-hexane:acetone=2:2:1) to give 1-(6,7-dipropoxy-1,2-dihydro-3-naphthoyl)-4-(3,4,5-trimethoxybenzoyl)piperazine (1.4 g). This product is recrystallized from a mixture of ethyl acetate and hexane to afford colorless needles, m.p. 124°–126° C.

Elemental Analysis for $C_{31}H_{40}N_2O_7$: Calcd.: C 67.37; H 7.30; N 5.07. Found: C 67.49; H 7.33; N 5.05.

EXAMPLE 67

A mixture of 6,7-dimethoxy-1,2-dihydro-3-naphthoic acid (0.8 g), thionyl chloride (2.0 ml) and toluene (10 ml) is heated under reflux for one hour. The reaction mixture is concentrated under reduced pressure. To the residue is added toluene (10 ml), and the mixture is again concentrated under reduced pressure. Thus-obtained 6,7-dimethoxy-1,2-dihydro-3-naphthoyl chloride is dissolved in methylene chloride (8 ml). The solution is added dropwise in the course of three minutes, with stirring under ice-cooling, to a mixture of 1-(3,4dimethoxybenzoyl)piperazine hydrochloride (1.03 g), triethylamine (1.1 g) and methylene chloride (18 ml). The resulting mixture is stirred at room temperature for two hours. To the reaction mixture is added water (50 ml), then the methylene chloride layer is separated. The aqueous layer is extracted with methylene chloride (15 ml). The methylene chloride layers are combined, washed with water, dried and concentrated under reduced pressure. The residue is purified by silica gel column chromatography (ethyl acetate:acetone:hexane=10:8:5) to obtain 1-(6,7-dimethoxy-1,2-dihydro-3-naphthoyl)-4-(3,4-dimethoxybenzoyl)piperazine (1.5 g). The product is recrystallized from ethyl acetate to give colorless needles, m.p. 190°–191° C.

Elemental Analysis for $C_{26}H_{30}N_2O_6$: Calcd.: C 66.94; H 6.48; N 6.00. Found: C 66.88; H 6.49; N 6.18.

EXAMPLE 68

A mixture of 6,7-dimethoxy-1,2-dihydro-3-naphthoic acid (0.8 g), thionyl chloride (2.0 ml) and toluene (10 ml) is heated for one hour under reflux. The reaction mixture is concentrated under reduced pressure. To the residue is added toluene (10 ml), and the mixture is again concentrated under reduced pressure. Thus-obtained 6,7-dimethoxy-1,2-dihydro-3-naphthoyl chloride is dissolved in methylene chloride (8 ml). The solution is added dropwise, with stirring under ice-cooling, in the course of three minutes, to a mixture of 1-(3,5-dimethoxybenzoyl)piperazine hydrochloride (1.03 g), triethylamine (1.1 g) and methylene chloride (8 ml). The resulting mixture is then stirred at room temperature for one hour. To the reaction mixture is added water (50 ml), and then the methylene chloride layer is separated. The aqueous layer is extracted with methylene chloride (15 ml). The methylene chloride layers are combined, washed with water, dried and concentrated under reduced pressure. The residue is purified by silica gel column chromatography (ethyl acetate:acetone:hexane=12:8:5) to afford 1-(6,7-dimethoxy-1,2-dihydro-3-naphthoyl)-4-(3,5-dimethoxybenzoyl)piperazine (1.4 g). This product is recrystallized from ethyl acetate to give colorless scales, m.p. 166°–167° C.

Elemental Analysis for $C_{28}H_{30}N_2O_6$: Cacld.: C 66.94; H 6.48; N 6.00. Found: C 66.84; H 6.57; N 5.88.

EXAMPLE 69

A mixture of 6,7-dimethoxy-1,2-dihydro-3-naphthoic acid (0.8 g), thionyl chloride (1.5 ml) and toluene (10 ml) is heated for one hour under reflux. The reaction mixture is concentrated under reduced pressure. To the residue is added toluene (8 ml), and the mixture is concentrated under reduced pressure. Thus-obtained 6,7-dimethoxy-1,2-dihydro-3-naphthoyl chloride is dissolved in methylene chloride (8 ml). The solution is added dropwise, with stirring under ice-cooling, in the course of 5 minutes, to a mixture of 1-(2,4,5-trimethoxybenzoyl)piperazine hydrochloride (1.15 g), triethylamine (1.1 g) and methylene chloride (18 ml). The resulting mixture is then stirred at room temperature for two hours. To the reaction mixture is added water (30 ml), and the methylene chloride layer is separated. The aqueous layer is extracted with methylene chloride (10 ml). The methylene chloride layers are combined, washed with water, dried and concentrated under reduced pressure. The residue is purified by silica gel column chromatography (ethyl acetate:hexane:ethanol=10:5:1) to afford 1-(6,7-dimethoxy-1,2-dihydro-3-naphthoyl)-4-(2,4,5-trimethoxybenzoyl)piperazine (1.5 g). This product is recrystallized from ethyl acetate to give colorless needles, m.p. 171°–172° C.

Elemental Analysis for $C_{27}H_{32}N_2O_7$: Calcd.: C 65.31; H 6.50; N 5.64. Found: C 65.55; H 6.51; N 5.66.

EXAMPLE 70

A mixture of 6,7-dimethoxy-1,2-dihydro-3-naphthoic acid (0.8 g), thionyl chloride (1.5 ml) and toluene (10 ml) is heated for one hour under reflux. The reaction mixture is concentrated under reduced pressure. To the residue is added toluene (8 ml), and the mixture is again concentrated under reduced pressure. Thus-obtained 6,7-dimethoxy-1,2-dihydro-3-napthoyl chloride is dissolved in methylene chloride (8 ml). The solution is added dropwise in the course of five minutes, with stirring under ice-cooling, to a mixture of 1-(2,3,4-trimethoxybenzoyl)piperazine hydrochloride (1.15 g), triethylamine (1.1 g) and methylene chloride (18 ml). The resulting mixture is then stirred at room temperature for two hours. To the reaction mixture is added water (30 ml), and the methylene chloride layer is separated. The aqueous layer is extracted with methylene chloride (10 ml). The methylene chloride layers are combined, washed with water, dried and concentrated under reduced pressure. The residue is treated with ethanol to give crystalline solid which is collected by filtration. This product is recrystallized from ethyl acetate to give 1-(6,7-dimethoxy-1,2-dihydro-3-naphthoyl)-4-(2,3,4-trimethoxybenzoyl)piperazine (1.2 g) as colorless powdery crystals, m.p. 166°–167° C.

Elemental Analysis for $C_{27}H_{32}N_2O_7$: Calcd.: C 65.31; H 6.50; N 5.64. Found: C 65.52; H 6.52; N 5.66.

EXAMPLE 71

A mixture of 2,3-dimethoxy-6,7-dihydro-5H-benzocycloheptene-8-carboxylic acid (0.5 g), thionyl chloride (1 ml), and toluene (10 ml) is heated for one hour under reflux. The reaction mixture is concentrated under reduced pressure. To the residue is added toluene (10 ml), and the mixture is again concentrated under reduced pressure. Thus-obtained 2,3-dimethoxy-6,7-dihydro-5H-benzocycloheptene-8-carbonyl chloride is dissolved in methylene chloride (6 ml). The solution is then added dropwise in the course of three minutes, with stirring under ice-cooling, to a mixture of 1-(3,4,5-triethoxybenzoyl)piperazine hydrochloride (0.75 g), triethylamine (1.0 g) and methylene chloride (10 ml). The resulting mixture is then stirred at room temperature for 1.5 hours. To the reaction mixture is added water (30 ml), and the methylene chloride layer is separated. The aqueous layer is extracted with methylene chloride (15 ml). The methylene chloride layers are combined, washed with water, dried and concentrated under reduced pressure. The residue is purified by silica gel column chromatography (hexane:ethyl acetate:ethanol=10:10:1) to afford 1-(2,3-dimethoxy-6,7-dihydro-5H-benzocyclohepten-8-ylcarbonyl)-4-(3,4,5-triethoxybenzoyl)piperazine (0.95 g). This product is recrystallized from a mixture of ethyl acetate and hexane to give colorless needles, m.p. 125°–126° C.

Elemental Analysis for $C_{31}H_{40}N_2O_7 \cdot \frac{1}{4}H_2O$: Calcd.: C 66.82; H 7.33; N 5.03. Found: C 66.84; H 7.29; N 4.99.

EXAMPLE 72

A mixture of 2,3-diethoxy-6,7-dihydro-5H-benzocycloheptene-8-carboxylic acid (0.8 g), thionyl chloride (2.2 ml) and toluene (12 ml) is heated for one hour under reflux. The reaction mixture is concentrated under reduced pressure. To the residue is added toluene (10 ml), and the mixture is again concentrated under reduced pressure. Thus-obtained 2,3-diethoxy-6,7-dihydro-5H-benzocycloheptene-8-carbonyl chloride is dissolved in methylene chloride (6 ml). The solution is added dropwise in the course of three minutes, with stirring under ice-cooling, to a mixture of 1-(3,4,5-trimethoxybenzyl)piperazine hydrochloride (1.14 g), triethylamine (1.8 g) and methylene chloride (18 ml). The resulting mixture is stirred for one hour at room temperature. To the reaction mixture is added water (50 ml), and the methylene chloride layer is separated. The aqueous layer is extracted with methylene chloride (30 ml). The methylene chloride layers are combined, washed with water, dried and concentrated under reduced pressure. The residue is purified by silica gel column chromatography (eluent, hexane:ethyl acetate:acetone=2:2:1) to afford 1-(2,3-diethoxy-6,7-dihydro-5H-benzocyclohepten-8-ylcarbonyl)-4-(3,4,5-trimethoxybenzyl)piperazine (1.3 g). This product is recrystallized from ethyl acetate to give colorless needles, m.p. 133°–134° C.

Elemental Analysis for $C_{30}H_{40}N_2O_6$: Calcd.: C 68.68; H 7.68; N 5.34. Found: C 68.98; H 7.73; N 5.32.

This product (1.1 g) is converted to the hydrochloride in a mixture of ethanol and ethyl ether to give 1-(2,3-diethoxy-6,7-dihydro-5H-benzocyclohepten-8-ylcarbonyl)-4-(3,4,5-trimethoxybenzyl)piperazine hydrochloride (1.1 g) as colorless crystals, m.p. 182°–184° C.

Elemental Analysis for $C_{30}H_{40}N_2O_6 \cdot HCl$: Calcd.: C 64.22; H 7.36; N 4.99. Found: C 63.97; H 7.37; N 4.87.

EXAMPLE 73

A mixture of 2,3-diethoxy-6,7-dihydro-5H-benzocycloheptene-8-carboxylic acid (0.8 g), thionyl chloride (2.2 ml) and toluene (12 ml) is heated for one hour under reflux. The reaction mixture is concentrated under reduced pressure. To the residue is added toluene (10 ml), and the mixture is again concentrated under reduced pressure. Thus-obtained 2,3-diethoxy-6,7-dihydro-5H-benzocyloheptene-8-carbonyl chloride is dissolved in methylene chloride (6 ml). The solution is added dropwise in the course of three minutes, with stirring under ice-cooling, to a mixture of 1-(3,4,5-trimethoxybenzoyl)piperazine hydrochloride (1.0 g), triethylamine (1.1 g) and methylene chloride (15 ml). The resulting mixture is stirred at room temperature for 1.5 hour. To the reaction mixture is added water (30 ml), and the methylene chloride layer is separated. The aqueous layer is extracted with methylene chloride (20 ml). The methylene chloride layers are combined, washed with water, dried and concentrated under reduced pressure. The residue is purified by silica gel column chromatography (eluent, ethyl acetate:hexane:acetone=12:8:5) to afford 1-(2,3-diethoxy-6,7-dihydro-5H-benzocyclohepten-8-ylcarbonyl)-4-(3,4,5-trimethoxybenzoyl)piperazine (1.45 g). This product is recrystallized from ethyl acetate to give colorless needles, m.p. 183°–185° C.

Elemental Analysis for $C_{30}H_{38}N_2O_7$: Calcd.: C 66.90; H 7.11; N 5.20. Found: C 66.78; H 7.13; N 5.13.

EXAMPLE 74

A mixture of 2,3-dimethoxy-6,7-dihydro-5H-benzocycloheptene-8-carboxylic acid (1.8 g), thionyl chloride (3 ml) and toluene (30 ml) is heated for one hour under reflux. The reaction mixture is concentrated under reduced pressure. The concentrate is dissolved in methylene chloride (25 ml). The solution is added dropwise, with stirring under ice-cooling, to a mixture of 1-formyl piperazine (2.0 g) and methylene chloride (30 ml). The reaction mixture is stirred for two hours. After addition of water, the mixture is extracted with methylene chloride. The organic layer is washed with water, dried and concentrated under reduced pressure. Methanol (60 ml) and 3N hydrochloric acid (60 ml) are added to the residue, and the mixture is heated for three hours under reflux. The reaction mixture is concentrated under reduced pressure, and the concentrate is subjected to extraction with ethyl acetate. The aqueous layer is made alkaline with sodium hydroxide, followed by extraction with methylene chloride. The organic layer is washed with water, dried and concentrated under reduced pressure. The residue is recrystallized from ethyl acetate to afford 1-(2,3-dimethoxy-6,7-dihydro-5H-benzocyclohepten-8-ylcarbonyl)piperazine as colorless needles (1.2 g), m.p. 137°–138° C.

Elemental Analysis for $C_{18}H_{24}N_2O_3 \cdot \frac{1}{2}H_2O$: Calcd.: C 66.44; H 7.74; N 8.61. Found: C 66.49; H 7.73; N 8.55.

EXAMPLE 75

To a mixture of 1-(2,3-dimethoxy-6,7-dihydro-5H-benzocyclohepten-8-ylcarbonyl)piperazine (1.2 g), triethylamine (0.5 g) and methylene chloride (20 ml) is added dropwise, with stirring under ice-cooling, a solution of 3,5-dimethoxy-4-ethoxybenzoyl chloride (1.0 g) in methylene chloride (20 ml). The reaction mixture is then stirred for one hour at room temperature, and then poured into ice-water, followed by extraction with methylene chloride. The organic layer is washed with water, dried and concentrated under reduced pressure. The concentrate is purified by silica gel column chromatography (hexane:ethyl acetate:acetone=1:2:1) to afford 1-(2,3-dimethoxy-6,7-dihydro-5H-benzocyclohepten-8-ylcarbonyl)-4-(3,5-dimethoxy-4-ethoxybenzoyl)piperazine (0.9 g). This product is recrystallized from ethyl acetatehexane to give colorless needles, m.p. 171°–172° C.

Elemental Analysis for $C_{29}H_{36}N_2O_7$: Calcd.: C 66.40; H 6.92; N 5.34. Found: C 66.21; H 6.89; N 5.25.

EXAMPLE 76

A mixture of 1-(3,4,5-trimethoxybenzoyl)piperazine (2.0 g), a Lawesson reagent [2,4-bis(4-methoxyphenyl)-1,3-dithia-2,4-diphosphethane-2,4-disulfide] (2.9 g) and benzene (20 ml) is heated for 30 minutes under reflux. 1N HCl (100 ml) and ethyl acetate are added to the reaction mixture. The mixture is shaken. The aqueous layer is separated, and treated with an aqueous solution of sodium hydroxide to make the system alkalline, followed by extraction with methylene chloride. The organic layer is washed with water, dried, and concentrated under reduced pressure. The residue is recrystallized from methylene chloride to give 1-(3,4,5-trimethoxythiobenzoyl)piperazine as pale yellow crystals (1.3 g), m.p. 116°–118° C.

Elemental Analysis for $C_{14}H_{20}N_2O_3S.\frac{3}{4}H_2O$: Calcd.: C 54.26; H 6.99; N 9.04. Found: C 54.39; H 6.72; N 9.03.

A mixture of 2,3-dimethoxy-6,7-dihydro-5H-benzocycloheptene-8-carboxylic acid (0.6 g), thionyl chloride (1 ml) and toluene (10 ml) is heated for one hour under reflux. The reaction mixture is concentrated under reduced pressure. A solution of the residue in methylene chloride (8 ml) is added dropwise, with stirring under ice-cooling, to a mixture consisting of 1-(3,4,5-trimethoxythiobenzoyl)piperazine (0.72 g), triethylamine (0.8 ml) and methylene chloride (10 ml). The mixture is stirred for 24 hours. After addition of water, the reaction mixture is shaken thoroughly. The organic layer is separated, washed with water, dried, and concentrated under reduced pressure. The residue is recrystallized from ethyl acetate to give 1-(2,3-dimethoxy-6,7-dihydro-5H-benzocyclohepten-8-ylcarbonyl)-4-(3,4,5-trimethoxythiobenzoyl)piperazine as pale yellow crystals (1.2 g), m.p. 172°–173° C.

Elemental Analysis for $C_{28}H_{34}N_2O_6S$: Calcd.: C 63.86; H 6.51; N 5.32. Found: C 63.59; H 6.54; N 5.31.

EXAMPLE 77

In a manner as that described in Example 62, 6,7-dimethoxy-2-naphthoic acid and 1-(3,4,5-trimethoxybenzoyl)piperazine are subjected to amidation to give 1-(6,7-dimethoxy-2-naphthoyl)-4-(3,4,5-trimethoxybenzoyl)piperazine. This product is recrystallized from ethyl acetate to give colorless needles, m.p. 224°–226° C.

Elemental Analysis for $C_{27}H_{30}N_2O_7$: Calcd.: C 65.57; H 6.11; N 5.66. Found: C 65.60; H 6.17; N 5.56.

EXAMPLE 78

In a manner as that described in Example 62, 3,4-dimethoxy-6,7-dihydro-5H-benzocycloheptene-8-carboxylic acid and 1-(3,4,5-trimethoxy-benzoyl)piperazine are subjected to amidation to give 1-(3,4-dimethoxy-6,7-dihydro-5H-benzocyclohepten-8-ylcarbonyl)-4-(3,4,5-trimethoxybenzoyl)piperazine. This product is recrystallized from ethyl acetate to give colorless prisms, m.p. 133°–134° C.

Elemental Analysis for $C_{28}H_{34}N_2O_7$: Calcd.: C 65.87; H 6.72; N 5.49. Found: C 65.84; H 6.79; N 5.52.

EXAMPLE 79

In methanol (20 ml) is dissolved 1-(6,7-dimethoxy-3,4-dihydro-3-naphthoyl)-4-(3,4,5-trimethoxybenzoyl)-piperazine (0.6 g). The solution is subjected to catalytic reduction in a stream of hydrogen in the presence of a 10% palladium-carbon (0.3 g). The reaction mixture is filtered off. The filtrate is concentrated under reduced pressure. To the concentrate is added ether, and the mixture is stirred. The resulting colorless powder is collected by filtration to afford 6,7-dimethoxy-1,2,3,4-tetrahydro-2-naphthoyl)-4-(3,4,5-trimethoxybenzoyl)-piperazine (0.5 g).

NMR-spectrum (CDCl₃) δ:1.7–3.1 ppm (6H, multiplet), 3.65 ppm (8H), 3.83 ppm (3H, singlet, OCH₃), 3.90 ppm (12H, singlet, OCH₃), 6.55 ppm (2H, singlet), 6.62 ppm (2H, singlet).

Elemental Analysis for $C_{27}H_{34}N_2O_7.\frac{1}{4}H_2O$: Calcd.: C 64.46; H 6.91; N 5.57. Found: C 64.33; H 6.74; N 5.73.

EXAMPLE 80

A mixture of 2,3-dibenzyloxy-6,7,8,9-tetrahydro-5H-benzocyclohepten-2-one (6.0 g), sodium methoxide (4.4 g) and dimethyl carbonate (80 ml) is heated under reflux in a stream of nitrogen for six hours. After cooling, water and dilute hydrochloric acid are added to the reaction mixture, and the acidic solution is extracted with ethyl acetate. The organic layer is washed with water, dried and subjected to concentration under reduced pressure to cause precipitation of crystals. This product is collected by filtration to obtain methyl ester of 2,3-dibenzyloxy-9-oxo-6,7,8,9-tetrahydro-5H-benzocycloheptene-8-carboxylic acid (6.7 g), m.p. 106°–108° C. (colorless needles: recrystallized from ethyl acetate-hexane)

Elemental Analysis for $C_{27}H_{26}O_5$: Calcd.: C 75.33; H 6.09. Found: C 75.36; H 5.89.

In a mixture of methylene chloride (80 ml) and methanol (100 ml) is dissolved the product obtained above. To the solution is added sodium borohydride (1.5 g) in limited amounts. To the reaction mixture is added water. The methylene chloride layer is separated, and the aqueous layer is extracted with methylene chloride. The organic layers are combined, washed with water and dried, followed by concentration under reduced pressure. Thus-obtained methyl ester of 2,3-dibenzyloxy-9-hydroxy-6,7,8,9-tetrahydro-5H-benzocycloheptene-8-carboxylic acid is dissolved in methanol (150 ml). To the solution is added 1N aqueous solution of sodium hydroxide (100 ml), and the mixture is stirred at 60° C. for 30 minutes. After cooling, concentrated hydrochloric acid (15 ml) is added to the reaction mixture, and the mixture is extracted with methylene chloride. The organic layer is concentrated under reduced pressure. To the residue is added dioxane (50 ml) and concentrated hydrochloric acid (4 ml), and the mixture is stirred at 80° C. for 15 minutes. After addition of water, the reaction mixture is extracted with ethyl acetate. The organic layer is washed with water, dried and concentrated under reduced pressure. The residue is recrystallized from ethyl acetate-hexane to give 2,3-dibenzyloxy-6,7-dihydro-5H-benzocycloheptene-8-carboxylic acid as colorless needles (3.75 g), m.p. 180°–181° C.

Elemental Analysis for $C_{26}H_{24}O_4$: Calcd.: C 77.98; H 6.04. Found: C 78.05; H 6.09.

EXAMPLE 81

A mixture of 2,3-dibenzyloxy-6,7-dihydro-5H-benzocycloheptene-8-carboxylic acid (3.0 g), thionyl chloride (4 ml) and toluene (40 ml) is heated for one hour under reflux. The reaction mixture is concentrated under reduced pressure. The resulting acid chloride dissolved in methylene chloride (30 ml) is added dropwise, with stirring under ice-cooling, to a mixture of 1-(3,4,5-trimethoxybenzoyl)piperazine (2.52 g), triethylamine (2.5 ml) and methylene chloride (50 ml). To the reaction mixture is added water, followed by extraction with methylene chloride. The organic layer is washed with water, dried and concentrated under reduced pressure. The residue is dissolved in ethyl acetate, washed with dilute hydrochloric acid and an aqueous solution of sodium hydrogencarbonate, dried and concentrated under reduced pressure. The residue is recrystallized from ethyl acetate-hexane to give 1-(2,3-dibenzyloxy-6,7-dihydro-5H-benzocyclohepten-8-ylcarbonyl)-4-(3,4,5-trimethoxybenzoyl)piperazine as colorless needles, m.p. 130°–132° C.

Elemental Analysis for $C_{40}H_{42}N_2O_7$: Calcd.: C 72.49; H 6.39; N 4.23. Found: C 72.38; H 6.46; N 4.22.

EXAMPLE 82

In acetic acid (40 ml) is dissolved 1-(2,3-dibenzyloxy-6,7-dihydro-5H-benzocyclohepten-8-ylcarbonyl)-4-(3,4,5-trimethoxybenzoyl)piperazine (4.0 g). To the solution is added an acetic acid solution of 30% hydrobromic acid (40 ml). The mixture is stirred at room temperature for one hour. To the reaction mixture is added water and ethyl acetate, and the mixture is shaken. The organic layer is washed with water and an aqueous solution of sodium hydrogencarbonate, dried and concentrated under reduced pressure. The residue is purified by silica gel column chromatography (eluent, acetone:ethyl acetate:hexane:methylene chloride=2:1:1:1) to give 1-(2,3-dihydroxy-6,7-dihydro-5H-benzocyclohepten-8-ylcarbonyl)-4-(3,4,5-trimethoxybenzoyl)piperazine (1.25 g). This product is recrystallized from ethyl acetate to give colorless crystals, m.p. 206°–207° C.

Elemental Analysis for $C_{26}H_{30}N_2O_7 \cdot \frac{1}{4}H_2O$: Calcd.: C 64.12; H 6.31; N 5.75. Found: C 64.22; H 6.15; N 5.73.

EXAMPLE 83

A mixture of 2,3-dimethoxy-5,6,7,8,9,10-hexahydrobenzocycloocten-5-one [R. Legros and P. Cangiant, Compt. Rend., 250, 147 (1960)] (0.8 g), sodium methoxide (0.34 g) and dimethyl carbonate (3.6 ml) is heated for two hours under reflux in a stream of nitrogen. The reaction mixture is cooled, and then poured into ice-water containing 1N HCl (20 ml), and the mixture is extracted with ethyl acetate. The organic layer is washed with water, dried and then concentrated under reduced pressure to afford methyl ester of 2,3-dimethoxy-5-oxo-5,6,7,8,9,10-hexahydrobenzocyclooctene-6-carboxylic acid as a pale yellow oily product (0.85 g). This product is dissolved in methanol (25 ml) and methylene chloride (15 ml). To the solution is added sodium borohydride (0.4 g) in limited amounts with stirring. The mixture is stirred for 1.5 hours. After addition of water (50 ml), the reaction mixture is shaken thoroughly. The organic layer is separated, and the aqueous layer is extracted with methylene chloride. The organic layers are combined and concentrated under reduced pressure. The residue is dissolved in a mixture of methanol (3 ml) and acetone (10 ml). To the solution is added a 1N aqueous solution of sodium hydroxide (10 ml), and the mixture is stirred at 60° C. for 10 minutes. The reaction mixture is cooled and then made acid with hydrochloric acid, and the mixture is extracted with ethyl acetate. The organic layer is concentrated under reduced pressure. To the residue is added dioxane (8 ml) and concentrated hydrochloric acid (3 ml), and the mixture is stirred at 90° C. for 30 minutes. After cooling, water (50 ml) is added to the reaction mixture, and the mixture is extracted with ethyl acetate. The organic layer is washed with water, dried and then concentrated under reduced pressure. Precipitating crystals are collected by filtration to give 2,3-dimethoxy-5,6,7,8-tetrahydrobenzocyclooctene-9-carboxylic acid (0.6 g). This product is recrystallized from ethyl acetate to give colorless needles, m.p. 200°–201° C.

Elemental Analysis for $C_{15}H_{18}O_4$: Calcd.: C 68.69; H 6.92. Found: C 68.56; H 6.99.

EXAMPLE 84

A mixture of 2,3-dimethoxy-5,6,7,8,-tetrahydrobenzocyclooctene-9-carboxylic acid (0.25 g), thionyl chloride (0.7 ml) and toluene (5 ml) is heated for one hour under reflux. The reaction mixture is concentrated under reduced pressure. To the residue is added toluene (5 ml), and the mixture is again concentrated under reduced pressure. The resulting 2,3-dimethoxy-5,6,7,8-tetrahydrobenzocyclooctene-9-carbonyl chloride is dissolved in methylene chloride (3 ml). The solution is added dropwise in the course of three minutes, with stirring under ice-cooling, to a mixture of 1-(3,4,5-trimethoxybenzyl)piperazine hydrochloride (0.37 g), triethylamine (0.58 g) and methylene chloride (8 ml). The mixture is then stirred at room temperature for one hour. To the reaction mixture is added water (30 ml), and the methylene chloride layer is separated. The aqueous layer is extracted with methylene chloride (10 ml). The methylene chloride layers are combined washed with water, dried and concentrated under reduced pressure. The residue is purified by silica gel column chromatography (hexane:ethyl acetate:ethanol=10:15:2) to give 1-(2,3-dimethoxy-5,6,7,8-tetrahydrobenzocyclooten-9-ylcarbonyl)-4-(3,4,5-trimethoxybenzoyl)piperazine as a colorless oily product (0.45 g).

In a mixture of ethanol and ethyl ether, the above product (0.45 g) is converted to the hydrochloride to give 1-(2,3-dimethoxy-5,6,7,8-tetrahydrobenzocycloocten-9-ylcarbonyl)-1-(3,4,5-trimethoxybenzyl)piperazine hydrochloride (0.45 g) as colorless prisms, m.p. 200°–203° C.

Elemental Analysis for $C_{29}H_{38}N_2O_6 \cdot HCl$: Calcd.: C 63.67; H 7.19; N 5.12. Found: C 63.67; H 7.20; N 5.03.

EXAMPLE 85

A mixture of 2,3-dimethoxy-5,6,7,8-tetrahydrobenzocyclooctene-9-carboxylic acid (0.3 g), thionyl chloride (0.8 ml) and toluene (6 ml) is heated for one hour under reflux. The reaction mixture is concentrated under reduced pressure. To the residue is added toluene (5 ml), and the mixture is again concentrated under reduced pressure. Thus-obtained 2,3-dimethoxy-5,6,7,8-tetrahydrobenzocyclooctene-9-carbonyl chloride is dissolved in methylene chloride (3 ml). The solution is added dropwise in the course of three minutes, with stirring under ice-cooling, to a mixture of 1-(3,4,5-trimethoxybenzoyl)piperazine hydrochloride (0.4 g), triethylamine (0.43 g) and methylene chloride (8 ml), and the mixture is then stirred for two hours at room temperature. To the reaction mixture is added water (20 ml), and the methylene chloride layer is separated. The aqueous layer is extracted with methylene chloride (10 ml). The methylene chloride layers are combined, washed with water, dried and then concentrated under reduced pressure. The residue is purified by silica gel column chromatography (ethyl acetate:hexane:ethanol=15:10:2) to give 1-(2,3-dimethoxy-5,6,7,8-tetrahydrobenzocycloocten-9-ylcarbonyl)-4-(3,4,5-trimethoxybenzoyl)piperazine (0.47 g). This product is recrystallized from a mixture of ethyl acetate and hexane to give colorless prisms, m.p. 170°–171° C.

Elemental Analysis for $C_{29}H_{36}N_2O_7$: Calcd.: C 66.40; H 6.92; N 5.34. Found: C 66.50; H 7.00; N 5.28.

EXAMPLE 86

To a solution of 1-(2,3-dimethoxy-6,7-dihydro-5H-benzocyclohepten-8-ylcarbonyl)-4-(3,4,5-trimethoxybenzoyl)piperazine (1.0 g) obtained in Example 62 in ethanol (50 ml) is added 10% palladium-carbon (50 mg), followed by catalytic reduction in a stream of hydrogen. The reaction mixture is filtered off, and the filtrate is concentrated under reduced pressure. To the residue is added ether, and the mixture is stirred to obtain 1-(2,3-dimethoxy-5,6,7,8-tetrahydrobenzocyclohepten-6-ylcarbonyl)-4-(3,4,5-trimethoxy-benzoyl)piperazine as a colorless powder.

NMR-spectrum (CDCl$_3$) δ: 1.80–2.25 ppm (4H, multiplet), 2.50–3.28 ppm (5H, multiplet), 3.33–3.80 ppm (8H, multiplet), 3.85 ppm (15H, singlet, OCH$_3$), 6.59 ppm (2H, singlet), 6.63 ppm (2H, singlet).

IR-spectrum $v_{max}^{KBr}$ cm$^{-1}$: 2950, 1650, 1590.

EXAMPLE 87

A mixture of 2,3-dihydroxy-6,7,8,9-tetrahydro-5H-benzocyclohepten-5-one (10 g), benzyl chloride (8 g), anhydrous potassium carbonate (9 g) and acetone (200 ml) is stirred at 50° C. for two hours. The reaction mixture is cooled and filtered off. The filtrate is concentrated under reduced pressure. The concentrate is dissolved in ethyl acetate. The organic layer is washed with water, dried and concentrated under reduced pressure. The residue is purified by silica gel column chromatography (eluent, hexane:ethyl acetate:methylene chloride=3:1:1) to afford 2-benzyloxy-3-hydroxy-6,7,8,9-tetrahydro-5H-benzocyclohepten-5-one (8.8 g). This product is recrystallized from ethyl acetate-hexane to give colorless needles, m.p. 127°–128° C.

Elemental Analysis for $C_{18}H_{18}O_3$: Calcd.: C 76.57; H 6.43. Found: C 76.39; H 6.44.

A mixture of the above product (5.0 g), dimethyl sulfate (3.4 g), anhydrous potassium carbonate (5.0 g) and N,N-dimethylformamide (60 ml) is stirred at 80° C. for 24 hours. To the reaction mixture is added water, followed by extraction with ethyl acetate. The organic layer is washed with dilute hydrochloric acid, sodium hydrogencarbonate and water, successively, dried and then concentrated under reduced pressure. The residue is purified by silica gel column chromatography (eluent, hexane:ethyl acetate=2:1) to give 2-benzyloxy-3-methoxy-6,7,8,9-tetrahydro-5H-benzocyclohepten-5-one (4.5 g). This product is recrystallized from ethyl acetate-hexane to give colorless needles, m.p. 95°–96° C.

Elemental Analysis for $C_{19}H_{20}O_3$: Calcd.: C 77.00; H 6.80. Found: C 76.98; H 6.83.

Subsequently, a mixture of the above product (2.5 g), sodium methoxide (2.3 g) and dimethyl carbonate (60 ml) is heated for five hours under reflux. The reaction mixture is poured into ice-water containing concentrated hydrochloric acid (6 ml), and then extracted with ethyl acetate. The organic layer is washed with water, dried and concentrated under reduced pressure to leave methyl ester of 2-benzyloxy-3methoxy-5-oxo-6,7,8,9-tetrahydro-5H-benzocycloheptene-6-carboxylic acid as a reddish brown oily product (2.8 g).

IR-spectrum $v_{max}^{neat}$ cm$^{-1}$: 1740, 1640, 1600, 1510, 1440, 1370, 1240, 1210, 1130, 1100, 1020.

To a solution of the above product (2.7 g) dissolved in a mixture of methylene chloride (60 ml) and methanol (70 ml) is added sodium borohydride (0.6 g) in limited amounts at room temperature with stirring. The mixture is stirred for one hour. After addition of water, the reaction mixture is extracted with methylene chloride. The organic layer is concentrated under reduced pressure. To a solution of the residue in methanol (50 ml) is added a 10% aqueous solution of sodium hydroxide (10 ml), and the mixture is stirred at 60° C. for 30 minutes. The reaction mixture is cooled and, then, methanol is distilled off under reduced pressure. The aqueous layer is made acid with 10% hydrochloric acid, followed by extraction with methylene chloride. The organic layers are combined and concentrated under reduced pressure. To the residue are added dioxane (30 ml) and concentrated hydrochloric acid (1 ml), and the mixture is stirred at 80° C. for one hour. After cooling and subsequent addition of water, the reaction mixture is extracted with ethyl acetate. The organic layer is washed with water, dried and then concentrated under reduced pressure. To the residue is added ether, and the resulting precipitates are collected by filtration to give 3-benzyloxy-2-methoxy-6,7-dihydro-5H-benzocycloheptene-8-carboxylic acid (1.8 g). This product is recrystallized from ethyl acetate to give colorless crystals, m.p. 163°–165° C.

Elemental Analysis for $C_{20}H_{20}O_4 \cdot \frac{1}{3}H_2O$: Calcd.: C 72.71; H 6.31. Found: C 72.56; H 6.20.

EXAMPLE 88

A mixture of 3-benzyloxy-2-methoxy-6,7-dihydro-5H-benzocycloheptene-8-carboxylic acid (1.5 g), thionyl chloride (1.5 ml) and toluene (12 ml) is heated for one hour under reflux. The reaction mixture is cooled and, then concentrated under reduced pressure. A solution of the residue in methylene chloride (8 ml) is added dropwise, with stirring under ice-cooling, to a mixture of 1-(3,4,5-trimethoxybenzoyl)piperazine (1.7 g), triethylamine (1.3 ml) and methylene chloride (15 ml). The mixture is stirred for two hours. After addition of water, the reaction mixture is extracted with methylene chloride. The organic layer is washed with dilute hydrochloric acid, an aqueous solution of sodium hydrogencarbonate and water, successively, dried and concentrated under reduced pressure. The residue is recrystallized from ethyl acetate to give 1-(3-benzyloxy-2-methoxy-6,7-dihydro-5H-benzocyclohepten-8-ylcarbonyl)-4-(3,4,5-trimethoxybenzoyl)piperazine (2.4 g) as colorless plates, m.p. 140°-142° C.

Elemental Analysis for $C_{34}H_{38}N_2O_7 \cdot H_2O$: Calcd.: C 67.53; H 6.67; N 4.63. Found: C 67.63; H 6.74; N 4.51.

EXAMPLE 89

A mixture of 1-(3-benzyloxy-2-methoxy-6,7-dihydro-5H-benzocyclohepten-8-ylcarbonyl)-4-(3,4,5-trimethoxybenzoyl)piperazine (1.7 g), a 30% acetic acid solution of hydrobromic acid (6 ml) and acetic acid (12 ml) is stirred at room temperature for 40 minutes. To the reaction mixture is added ether (100 ml), and the resulting precipitates are collected by filtration. To the precipitates are added ethyl acetate and water. The mixture is shaken, then the organic layer is separated. The organic layer is washed with an aqueous solution of sodium hydrogencarbonate, and water, and dried, followed by distilling off the solvent under reduced pressure. The residue is purified by silica gel column chromatography (eluent, hexane:ethyl acetate:acetone:methylene chloride=1:1:1:1) to give 1-(3-hydroxy-2-methoxy-6,7-dihydro-5H-benzocyclohepten-8-ylcarbonyl)-4-(3,4,5-trimethoxybenzoyl)piperazine (1.2 g). Recrystallization of this product from ethyl acetate affords colorless crystals, m.p. 198°-199° C.

Elemental Analysis for $C_{27}H_{32}N_2O_7$: Calcd.: C 65.31; H 6.50; N 5.64. Found: C 65.25; H 6.51; N 5.86.

EXAMPLE 90

A mixture of 2,3-dihydroxy-6,7,8,9-tetrahydro-5H-benzocyclohepten-5-one (1.0 g), dimethyl sulfate (0.65 g), anhydrous potassium carbonate (0.86 g) and acetone (20 ml) is stirred at 50° C. for two hours. After cooling, the reaction mixture is subjected to filtration, and the filtrate is concentrated under reduced pressure. To the concentrate is added water, which is extracted with ethyl acetate. The organic layer is washed with water, dried and concentrated under reduced pressure. The residue is purified by silica gel column chromatography (hexane:ethyl acetate=5:1) to afford 3-hydroxy-2-methoxy-6,7,8,9-tetrahydro-5H-benzocyclohepten-5-one (0.67 g), which is recrystallized from ethyl acetate-hexane to give colorless needles, m.p. 115°-116° C.

Elemental analysis for $C_{12}H_{14}O_3$: Calcd.: C 69.89; H 6.84. Found: C 69.79; H 6.80.

A mixture of 3-hydroxy-2-methoxy-6,7,8,9-tetrahydro-5H-benzocyclohepten-5-one (2.5 g), benzyl chloride (1.84 g), anhydrous potassium carbonate (2.5 g) and N,N-dimethylformamide (20 ml) is stirred at 80° C. for three hours. The reaction mixture is poured into ice-water, followed by extraction with ethyl acetate. The organic layer is washed with water, dried and concentrated under reduced pressure. The concentrate is purified by silica gel column chromatography (hexane:ethyl acetate=4:1) to afford 3-benzyloxy-b 2-methoxy-6,7,8,9-tetrahydro-5H-benzocyclohepten-5-one (3.3 g) as crystals. This product is recrystallized from ethyl acetate-hexane to give colorless needles, m.p. 64°-65° C.

Elemental Analysis for $C_{19}H_{20}O_3$: Calcd.: C 77.00; H 6.80. Found: C 77.21; H 6.84.

A mixture of 3-benzyloxy-2-methoxy-6,7,8,9-tetrahydro-5H-benzocyclohepten-5-one (3.2 g), sodium methoxide (2.8 g) and dimethyl carbonate (100 ml) is heated for four hours under reflux in a stream of nitrogen. The reaction mixture is poured into ice-water containing concentrated hydrochloric acid (10 ml), and extracted with ethyl acetate. The organic layer is washed with water, dried and concentrated under reduced pressure to afford 3-benzyloxy-2-methoxy-5-oxo-6,7,8,9-tetrahydro-5H-benzocycloheptene-6-carboxylic acid methyl ester (3.7 g) as a pale yellow oily product.

Elemental Analysis for $C_{21}H_{22}O_5$: Calcd.: C 71.17; H 6.26. Found: C 71.43; H 6.12.

The above-obtained oily product (3.6 g) is dissolved in a mixture of methanol (80 ml) and methylene chloride (60 ml). To the solution is added in limited amounts sodium borohydride (0.6 g) with stirring. The mixture is stirred for two hours. After addition of water, the mixture is shaken. The organic layer is separated and concentrated under reduced pressure. The concentrate is dissolved in methanol (50 ml), to which is added a 2N aqueous solution of sodium hydroxide (30 ml), followed by stirring at 60° C. for 30 minutes. Methanol is distilled off under reduced pressure, and the reaction mixture is made acid with dilute hydrochloric acid, which is extracted with methylene chloride. The organic layer is concentrated under reduced pressure. To the concentrate are added dioxane (30 ml) and concentrated hydrochloric acid (2 ml). The mixture is stirred at 90° C. for 10 minutes. The reaction mixture is poured into ice-water, followed by extraction with ethyl acetate. The organic layer is washed with water, dried and concentrated under reduced pressure to afford crude crystals, followed by recrystallization from ethyl acetate to give 2-benzyloxy-3-methoxy-6,7-dihydro-5H-benzocycloheptene-8-carboxylic acid (2.4 g) as colorless needles, m.p. 172°-173° C.

Elemental Analysis for $C_{20}H_{20}O_4$: Calcd.: C 74.06; H 6.21. Found: C 73.88; H 6.24.

EXAMPLE 91

A mixture of 2-benzyloxy-3-methoxy-6,7-dihydro-5H-benzocycloheptene-8-carboxylic acid (1.5 g), thionyl chloride (1.5 ml) and toluene (15 ml) is stirred at 100° C. for one hour. The reaction mixture is concentrated under reduced pressure. The concentrate is dissolved in methylene chloride (10 ml). The solution is added dropwise, with stirring under ice-cooling, to a mixture of 1-(3,4,5-trimethoxybenzoyl)piperazine (1.7 g), triethylamine (1.3 ml) and methylene chloride (20 ml). The reaction mixture is stirred at room temperature for one hour. The mixture is poured into ice-water, followed by extraction with methylene chloride. The organic layer is washed with 1N HCl, an aqueous solution of sodium hydrogencarbonate and water, which is dried and then concentrated under reduced pressure. The concentrate is purified by silica gel column chromatography (hexane:ethyl acetate:acetone=5:4:3) to afford 1-(2-benzyloxy-3-methoxy-6,7-dihydro-5H-benzocylcohepten-8-ylcarbonyl)-4-(3,4,5-trimethoxybenzoyl)piperazine (2.4 g) as colorless crystals. This product is recrystallized from ethyl acetate to give colorless needles, m.p. 151°-152° C.

Elemental Analysis for $C_{34}H_{38}N_2O_7$: Calcd.: C 69.61; H 6.53; N,4.77. Found: C 69.43; H 6.57; N,4.77.

EXAMPLE 92

To a solution of 1-(2-benzyloxy-3-methoxy-6,7-dihydro-5H-benzocyclohepten-8-ylcarbonyl)-4-(3,4,5-trimethoxybenzoyl)piperazine (2.0 g) in acetic acid (12 ml) is added a 30% acetic acid solution of hydrobromic acid (8 ml), and the mixture is left standing for three hours at room temperature. To the reaction mixture is added ethyl ether (120 ml), and then resulting precipitates are collected by filtration. To the precipitates thus-obtained are added ethyl acetate and water, and the mixture is shaken. The organic layer is separated, washed with an aqueous solution of sodium hydrogencarbonate, dried and concentrated under reduced pressure. The concentrate is purified by silica gel column chromatography (hexane:ethyl acetate:acetone: methylene chloride=1:2:1:1:), followed by crystallization from ethyl acetate to afford 1-(2-hydroxy-3-methoxy-6,7-dihydro-5H-benzocyclohepten-8-ylcarbonyl)-4,-(3,4,5-trimethoxybenzoyl)piperazine (1.36 g) as colorless needles, m.p. 192°–193° C.

Elemental Analysis for $C_{27}H_{32}N_2O_7$: Calcd.: C 65.31; H 6.50; N,5.64. Found: C 65.01; H 6.50; N,5.64.

FORMULATION EXAMPLE 1

A mixture of 1-(2,3-dimethoxy-6,7-dihydro-5H-benzocyclohepten-8-ylcarbonyl)-4-(3,4,5-trimethoxybenzoyl)piperazine (10 g), lactose (90 g) and corn starch (17 g) is granulated with a paste prepared from corn starch (7 g), to which are added corn starch (5 g) and magnesium stearate (1 g). The mixture is blended and formulated into compressed tablets (1000 tablets).

The compounds (I) of the present invention and their salts are excellent in absorption from the intestinal canal and show excellent PAF antagonism even by oral administration. Therefore, the compounds (I) and their salts can be administered not only non-orally such as by injection, but also orally.

The following test examples explain the effects of this invention more concretely.

TEST EXAMPLE 1

Inhibitory Action on PAF-Induced Platelet Aggregation

Blood was collected from the hearts of conscious New Zealand white male rabbits weighing 2 to 3 kg using citric acid as an anticoagulant (one volume part of 3.15% citric acid per 9 volume parts of the whole blood). The blood was subjected to a centrifuge at 800 rpm for ten minutes to obtain platelet rich plasma (PRP). The remaining blood after collecting the PRP was subjected to a centrifuge at 3000 rpm for ten minutes to obtain platelet poor plasma (PPP). PRP was diluted with PPP, and the number of platelets was adjusted to 500,000/µl. Platelet aggregation was examined by means of turbidimetry [Born, Nature, 194, 927–929 (1962)] with 8 channel aggregometer (NBS HEMA TRACER 6 Nikoh, Bioscience, Japan). More concretely, PRP (250 µl) was kept warm (37° C.) for three minutes in a silicon-processed cuvette, to which was added a test sample (25 µl) dissolved in a physiological saline or in 10mM dimethylsulfoxide followed by dilution with a physiological saline. Two minutes later, PAF (25 µl, $3\times10^{-9} - 1\times10^{-8}$M), dissolved in a physiological saline, was added and then the maximum aggregation rate was determined. As the control, physiological saline without test sample was added to the cuvette, and the inhibitory rate thereon was determined.

The results are shown in Table 1.

TABLE 1

| No. of Example of Drug | Platelet Aggregation Inhibitory Action(%) (Drug Concentration: $3 \times 10^{-5}$M) |
|---|---|
| 1 | 100 |
| 5 | 100 |
| 7 | 95 |
| 8 | 84 |
| 9 | 87 |
| 10 | 87 |
| 12 | 100 |
| 15 | 100 |
| 17 | 97 |
| 21 | 93 |
| 23 | 100 |
| 24 | 100 |
| 26 | 91 |
| 28 | 87 |
| 32 | 100 |
| 36 | 86 |
| 38 | 85 |
| 39 | 100 |
| 41 | 97 |
| 43 | 89 |
| 49 | 100 |
| 56 | 100 |
| 58 | 100 |
| 60 | 100 |
| 62 | 100 |
| 65 | 100 |
| 66 | 100 |
| 72 | 100 |
| 84 | 100 |
| 85 | 100 |

TEST EXAMPLE 2

Inhibitory Action on PAF-Induced Hypotension

SD (Jcl) male rats of 6 to 8 week old were subjected to the experiment. After fasting overnight, the rats were cannulated into the femoral artery and vein under anesthesia with pentobarbital. A transducer (MPU-0.5-2900-III, TOYO BALDWIN, Japan) was connected with the artery cannula, and blood pressure was continuously measured. When the blood pressure became constant, PAF (0.5 to 1.0 µg/kg, 250 µl/kg) dissolved in a physiological saline was injected through the venous cannula to lower the 30 to 45 mmHg of blood pressures. After 30 minutes, PAF was injected again, and the average of lowered values of blood pressure (twice) was used as the control. After restoration of blood pressure, the test samples prepared by dissolving or suspending the drug in a physiological saline suspension of gum arabic (5%) were orally administered (5 ml/kg), then, after 1,2 and 4 hours, PAF was injected. The rate of inhibition of lowering of blood pressure after administration of the test samples against the control was evaluated. The results are shown in Table 2.

TABLE 2

| No. of Example of Drug | Dosage (mg/kg) p.o. | Inhibitory action on PAF-Induced Hypotension (%) | | |
|---|---|---|---|---|
| | | After 1 hr. | After 2 hrs. | After 4 hrs. |
| 5 | 30 | 77 | 75 | 49 |
| 39 | 30 | 70 | 64 | 47 |
| 49 | 30 | 94 | 97 | 88 |
| 56 | 30 | 100 | 97 | 88 |
| 58 | 30 | 88 | 95 | 65 |
| 60 | 30 | 79 | 69 | 60 |
| 61 | 30 | 86 | 82 | 74 |
| 62 | 30 | 100 | 100 | 100 |
| 65 | 30 | 100 | 100 | 77 |

TABLE 2-continued

| No. of Example of Drug | Dosage (mg/kg) p.o. | Inhibitory action on PAF-Induced Hypotension (%) | | |
|---|---|---|---|---|
| | | After 1 hr. | After 2 hrs. | After 4 hrs. |
| 66 | 30 | 77 | 79 | 68 |
| 72 | 30 | 98 | 99 | 75 |
| 73 | 30 | 98 | 98 | 96 |
| 75 | 30 | 61 | 54 | 61 |
| 76 | 30 | 100 | 100 | 100 |
| 76 | 3 | 72 | 69 | 60 |
| 78 | 30 | 73 | 57 | 26 |
| 79 | 30 | 81 | 88 | 66 |
| 84 | 30 | 100 | 100 | 73 |
| 85 | 30 | 100 | 100 | 100 |
| 86 | 30 | 100 | 100 | 100 |
| 86 | 10 | 90 | 92 | 92 |

TEST EXAMPLE 3

Anti-Endotoxin Shock Activity in Rats

[Method]

In a manner similar to that described in Test Example 2, Jcl: SD male rats (200 to 250 g) were applied with cannulation for measurement of blood pressure and for injecting PAF. The test animals were fasted overnight, and the experiments were conducted. The cannula on the side of femoral artery was connected with a pressure transducer and secured. The, endotoxin (ET) (50 mg/kg) was given through the cannula on the side of femoral vein at a rate of 1 ml/kg. While measuring blood pressure continuously, time until death was measured. Test drugs (30 mg/kg) were suspended in gum arabic and water, which were orally administered (5 ml/kg) to test animals one hour before the injection of ET. The animals in the control group were administered with a suspension of gum arabic in water.

[Results]

The results are shown in Tables 3 and 4. The test drug orally administered (30 mg/kg) suppressed significantly the lowering of blood pressure due to ET. (survival time, control group: 108±26 minutes, test drug, 30 mg/kg, p.o. group: 320±45 minutes**).

TABLE 3

| | Activity against ET-induced hypotension in rats | | | | | |
|---|---|---|---|---|---|---|
| | Blood Pressure (mmHg) | | | | | |
| Test Drug | 0 | 3 | 5 | 10 | 15 | 20 (min.) |
| Control Group (n = 7) | 95 ± 3 | 74 ± 7 | 65 ± 5 | 67 ± 8 | 70 ± 10 | 77 ± 9 |
| Oral administration of the compound of Example 62 (30 mg/kg) one hour before test (n = 5) | 92 ± 2 | 82 ± 6 | 90 ± 4** | 90 ± 4* | 92 ± 3 | 95 ± 3 |

*P < 0.05, **P < 0.01

TABLE 4

| | Preventive effevt against ET-induced death in rats | | | | | | | | |
|---|---|---|---|---|---|---|---|---|---|
| | Number of survivals | | | | | | | | |
| Test Drug | 0 | 1 | 2 | 3 | 4 | 5 | 6 | 7 | 8 (hr) |
| Control Group (n = 7) | 7 | 5 | 3 | 1 | 0 | | | | |
| Oral administration of the compound of Example 62 (30 mg/kg) one hour before test (n = 5) | 5 | 5 | 5 | 5 | 4 | 2 | 1 | 1 | 1 |

TEST EXAMPLE 4

Inhibitory Action Against Reversed Passive Arthus Reaction

[Method]

This reaction was conducted, in accordance with the method reported by Chang and Otterness [Eur. J. Pharmacol., 69, 155 (1981)], by using rabbit anti-egg albumin (EA) antiserum. Jcl SD male rats (7 wk) were used. Under ether anesthesia, the hair of the back was cut and 1 ml of a 0.5% solution of EA in physiological saline was injected into the tail vein, followed by intracutaneous injection of 0.1 ml each of the left- and right-hand sides of the back. Vascular permeability was measured as follows. Three hours later, 1 ml of physiological saline containing 1% of Evans blue was given intravenously, and 30 minutes later, the animals were sacrificed by bleeding and the skin excised, and the area of wheals stained with a leakage of the dye (major axis x minor axis, mm$^2$). The test compounds were suspended in a 5% gum arabic solution, which was administered orally one hour before administration of the antigen.

The results are shown in Table 5.

TABLE 5

| Action against reversed passive Arthus reaction | | | |
|---|---|---|---|
| Test Compound | Dose mg/kg, p.o. | Area of wheals stained with the dye (mm$^2$) | Preventive effect of reversed passive Arthus reaction (%) |
| Control | 5% gum arabic (n = 6) | 55.3 ± 5.6 | |
| Compound of Example 62 | 3.1 (n = 6) | 52.8 ± 2.7 | 5 |
| Compound of Example 62 | 12.5 (n = 6) | 38.4 ± 6.1 | 31 |
| Compound of Example 62 | 50 (n = 6) | 16.8 ± 5.1** | 70 |

**P < 0.01

TEST EXAMPLE 5

Action Against Diabetic Nephropathy

[Method]

Female KKAy mice of 10 weeks old were employed. Test animals were administered with the compound of Example 62 for three weeks at doses of 8 and 26 mg/kg/day in admixture with feedstuff. Then, urine was collected from these animals for 24 hours. Urine desalted (filtered urine) by means of a PD-10 column (Pharmacia) was employed to determine the total protein concentration in the urine by using a protein-assay kit (Bio-Rad). The amount ot albumin in the urine was calculated from the relative concentration of albumin to the total protein determined by means of electrophoresis.

Glucose and triglyceride in the plasma were determined by an enzyme method using the Ankol Chemistry System (Baker instruments).

[Results]

The compound of Example 62 suppressed the excretion of albumin in urine dose-dependently, and, at the dose of 26 mg/kg/day, the suppression was significant. The total protein in urine showed a tendency of being suppressed in a high dose. No change was obseerved in plasma glucose and triglyceride (Table 6).

TABLE 6

Action against diabetic nephopathy in mice

| Test Compound (No. Example | Dose mg/kg/day | N | Administration Route | Body Weight g | Amount of albumin (%) excreted in urine mg/day | Total amount of protein in urine mg/day |
|---|---|---|---|---|---|---|
| Control | | 8 | | 43.4 ± 0.6 | 15.0 ± 2.6 (54) | 27.6 ± 3.0 |
| 62 | 8 | 8 | p.o. | 44.8 ± 0.7 | 11.0 ± 2.0 (46) | 23.8 ± 2.9 |
| 62 | 26 | 8 | p.o. | 43.3 ± 0.5 | 8.0 ± 0.7* (36) | 22.0 ± 3.8 |

| Amount of glucose in plasma mg/dl | Amount of triglyceride in plasma mg/dl |
|---|---|
| 349 ± 29 | 547 ± 58 |
| 326 ± 26 | 499 ± 45 |
| 381 ± 33 | 546 ± 43 |

The drug was administered to female KKAy mice (10 wk-old) for 3 weeks.

The values are the means ±SE.*, p<0.05 vs control.

TEST EXAMPLE 6

Action Against Experimental Cerebral Infarction in Mongolian Gerbils

[Method]

Male 10 weeks old Mongolian gerbils were anesthetized with ether. The common carotid artery on both sides was exposed surgically. After waking, the artery was ligated with steel clips for 15 minutes. Then, the clips were removed and the blood was reperfused for three hours. Ataxia symptoms and manifestations of neuro-deficiency were assessed by the method using stroke index [C. P. McGraw: Arch. Neurol., 34, 334–336 (1977)] and inclined plane [A. S. Rivlin et al.: J. Neurosurg., 47, 577–581 (1977)]. The test compounds were orally administered one hour before ligation as a suspension in gum arabic. The control group was administered with the same volume of gum arabic. The number of animals subjected to this experiment was 5 each in both groups.

TABLE 7

Effect of improving ataxia symptoms and manifestations of neurodeficiency due to cerebral infarction in Mongolian gerbils (stroke index)

| Times after ligation and reperfusion | Control group (n = 5) | Groups administered with the compound of Example 62 (30 mg/kg, p.o.) (N = 5) |
|---|---|---|
| Ligation time (min.) | | |
| 0 | 0 | 0 |
| 15 | 18.0 ± 1.0 | 14.0 ± 1.0* |
| Time after reperfusion (min.) | | |
| 15 | 7.0 ± 0.4 | 4.2 ± 0.6** |

TABLE 7-continued

Effect of improving ataxia symptoms and manifestations of neurodeficiency due to cerebral infarction in Mongolian gerbils (stroke index)

| Times after ligation and reperfusion | Control group (n = 5) | Groups administered with the compound of Example 62 (30 mg/kg, p.o.) (N = 5) |
|---|---|---|
| 30 | 7.0 ± 0.4 | 3.4 ± 0.5** |
| 60 | 6.0 ± 0.6 | 3.2 ± 0.5** |
| 120 | 5.2 ± 0.7 | 2.0 ± 0** |
| 180 | 4.0 ± 0.5 | 0.8 ± 0.5** |

*P < 0.05,
**P < 0.01

TABLE 8

Effect of improving ataxia symptoms and manifestations of neurodeficiency due to cerebral infarction in Mongolian gerbils (inclined plane)

| Time after ligation and reperfusion | Angle (°) of inclined plane where test animals tumble down the ramp | |
|---|---|---|
| | Control group (n = 5) | Group administered with the compound of Example 62 (30 mg/kg, p.o.) (n = 5) |
| Ligation time (min.) | | |
| 0 | 49 ± 1 | 47 ± 1 |
| 15 | 20 ± 0 | 20 ± 0 |
| Time after reperfusion (min.) | | |
| 15 | 27 ± 2 | 34 ± 3 |
| 30 | 29 ± 2 | 35 ± 3 |
| 60 | 31 ± 1 | 35 ± 2* |
| 120 | 31 ± 1 | 36 ± 2* |
| 180 | 33 ± 1 | 38 ± 2 |

*P < 0.05

TEST EXAMPLE 7

Toxicity Test

[Method]

Male Wistar-strain rats (5 wk) were used in groups of five individuals. The animals of the respective groups were orally administered with the compound of Example 62 at the dose of 30, 100 and 300 mg/kg per day over a period of two weeks as a suspension in gum arabic and water at a rate of 10 ml/kg. The animals of the control group were administered with a suspension of gum arabic in water. [Results]

During the period of administration, no change was observed in general behaviors. Autopsy of the test animals revealed no abnormality in internal organs under macroscopic observation. No difference in body weight between the control group and the test group was observed.

What is claimed is:

1. A compound of the formula (I):

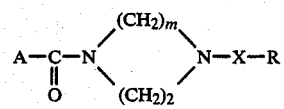

where A is a group selected from the class consisting of pentalenyl, indenyl, indanyl, naphthyl, dihydronaphthyl tetrahydronaphthyl, hexahydronaphthyl, azulenyl, heptalenyl, biphenylenyl, indacenyl, acenaphthylenyl, acenaphthenyl, phenalenyl, phenanthryl, dihydrophenanthryl, tetrahydrophenanthryl, hexahydrophenanthryl, anthryl, dihydroanthryl, tetrahydroanthryl, hexahydroanthryl, octahydroanthryl, fluorenyl, dihydrofluorenyl, tetrahydrofluorenyl, benzocycloheptenyl, tetrahydrobenzocycloheptenyl, dibenzocycloheptenyl, naphthocycloheptenyl, dihydronaphthocycloheptenyl, benzocyclooctenyl, dihydrobenzocyclooctenyl, tetrahydrobenzocyclooctenyl, hexahydrobenzocyclooctenyl and octahydrobenzocyclooctenyl, which may be substituted by one or two groups selected from the class consisting of a lower alkyl group, a halo lower alkyl group, a hydroxy lower alkyl group, a $C_{2-5}$ alkanoyloxy lower alkyl group, a benzoyloxy lower alkyl group, a lower alkoxy-lower alkyl group, a lower alkoxy group, a halo lower alkoxy group, a lower alkoxy carbonyl-lower alkoxy group, a lower alkenyloxy group, a phenyl lower alkyloxy group, a lower alkoxy-lower alkoxy group, a lower alkoxycarbonyl group, carboxyl group, carbamoyl group, an N,N-di-lower alkylcarbamoyl group, an N-lower alkyl carbamoyl group, a halo group, a cyano group, a nitro group, a hydroxy group, an $C_{2-5}$ alkanoyloxy group, a benzoyloxy group, an amino group, a lower alkylsulfonylamino group, a $C_{2-5}$ alkanoylamino group, a benzoylamino group, a lower alkoxycarbonylamino group, $C_{2-5}$ alkanoyl group, a benzoyl group, a mercapto, a lower alkylthio group, a lower alkylsulfinyl group, a lower alkylsulfonyl group and oxo group, R is a phenyl group substituted with one to five lower alkoxy groups; X is a methylene group, carbonyl group or thiocarbonyl group; and m is 2 or 3, or a pharmaceutically acceptable salt thereof.

2. A compound according to claim 1, wherein A is a hydrocarbon group of the formula:

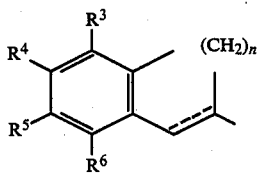

wherein the dotted line designates the presence or absence of a double bond; n is an integer of 1 to 4; and wherein two of the groups $R^3$, $R^4$, $R^5$ and $R^6$ are hydrogen and the other two are independently hydrogen, a lower alkyl group, a halo lower alkyl group, a hydroxy lower alkyl group, a $C_{2-5}$ alkanoyloxy lower alkyl group, a benzoyloxy lower alkyl group, a lower alkoxy-lower alkyl group, a lower alkoxy group, a halo lower alkoxy group, a lower alkoxy carbonyl-lower alkoxy group, a lower alkenyloxy group, a phenyl lower alkoxy group, a lower alkoxy-lower alkoxy group, a lower alkoxycarbonyl group, carboxyl group, carbamoyl group, an N,N-di-lower alkylcarbamoyl group, an N-lower alkyl carbamoyl group, halo group, cyano group, nitro group, hydroxy group, $C_{2-5}$alkanoyloxy group, a benzoyloxy group, amino group, a lower alkylsulfonylamino group, a $C_{2-5}$ alkanoylamino group, a benzoylamino group, a lower alkoxycarbonylamino grop, $C_{2-5}$ alkanoyl group, benzoyl group, mercapto group, a lower alkylthio group, a lower alkylsulfinyl group or a lower alkylsulfonyl group.

3. A compound according to claim 2, wherein two of the groups $R^3$, $R^4$, $R^5$ and $R^6$ are hydrogen and the other two are independently hydrogen, a lower alkoxy group, a phenyl lower alkoxy group, a lower alkoxy-lower alkoxy group, hydroxy group, $C_{2-5}$-alkanoyloxy or benzyloxy group.

4. A compound according to claim 3, wherein $R^3$ and $R^6$ are hydrogen.

5. A compound according to claim 4 wherein $R^4$ and $R^5$ are a lower alkoxy group.

6. A compound according to claim 5, wherein a lower alkoxy group is methoxy group or ethoxy group.

7. A compound according to claim 2, wherein n is 2 or 3.

8. A compound according to claim 2, wherein the dotted line designates the presence of double bond.

9. A compound according to claim 1, wherein m is 2.

10. A compound according to claim 9, wherein R is a phenyl group substituted with three lower alkoxy groups.

11. A compound according to claim 10, wherein R is a phenyl group of the formula:

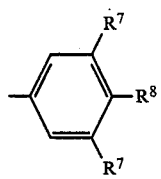

wherein $R^7$ and $R^8$ are independently methoxy group or ethoxy group.

12. A compound according to claim 11, wherein at least one of $R^7$ and $R^8$ is methoxy group, and the other is methoxy group or ethoxy group.

13. A compound according to claim 9, wherein R is a phenyl group of the formula:

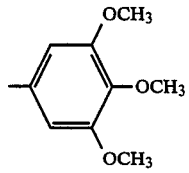

14. A compound according to claim 9, wherein X is methylene group.

15. A compound according to claim 9, wherein X is carbonyl group.

16. A compound according to claim 9, wherein X is thiocarbonyl group.

17. A compound according to claim 9, which is a compound of the formula:

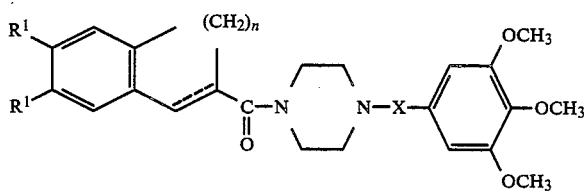

wherein
the dotted line designates the presence or absence of double bond;
n is an integer of 1 to 4; R¹ is a lower alkoxy group; and
X is methylene group, carbonyl group or thiocarbonyl group.

18. A compound according to claim 17, wherein X is methylene group or carbonyl group and the dotted line designates the presence of double bond.

19. A compound according to claim 9, which is 1-(2,3-dimethoxy-6,7-dihydro-5H-benzocyclohepten-8-ylcarbonyl)-4-(3,4,5-trimethoxybenzyl)piperazine.

20. A compound according to claim 9, which is 1-(6,7-dimethoxy-1,2-dihydro-3-naphthoyl)-4-(3,4,5-trimethoxybenzoyl)piperazine.

21. A compound according to claim 9, which is 1-(2,3-dimethoxy-6,7-dihydro-5H-benzocyclohepten-8-ylcarbonyl)-4-(3,4,5-trimethoxybenzoyl)piperazine.

22. A compound according to claim 9, which is 1-(2,3-dimethoxy-5,6,7,8-tetrahydrobenzocycloocten-9-ylcarbonyl)-4-(3,4,5-trimethoxybenzoyl)piperazine.

23. A compound according to claim 9, which is 1-(2,3-dimethoxy-5,6,7,8-tetrahydrobenzocyclohepten-6-ylcarbonyl)-4-(3,4,5-trimethoxybenzoyl)piperazine.

24. A pharmaceutical composition suitable for inhibiting activities of platelet activating factor which comprises
(a) as the active ingredient, an amount effective to inhibit activities of platelet activating factor of a compound as claimed in claim 1 or a pharmaceutically accepted salt thereof and
(b) a pharmaceutically acceptable carrier or excipient therefor.

25. A method for inhibiting activities of platelet activating factor in a mammal, which comprises administering to said mammal an amount effective to inhibit activities of platelet activating factor of a compound of claim 1 or a pharmaceutically acceptable salt thereof.

* * * * *

UNITED STATES PATENT AND TRADEMARK OFFICE
CERTIFICATE OF CORRECTION

PATENT NO. : 4,880,809

DATED : November 14, 1989

INVENTOR(S) : Hirosada SUGIHARA et al.

It is certified that error appears in the above-identified patent and that said Letters Patent is hereby corrected as shown below:

Column 57, lines 18-19, "dihydronaphthyl tetrahydronaphthyl" should be corrected to read --dihydronaphthyl, tetrahydronaphthyl--.

Column 57, line 26, "dihydrobenzocycloheptenyl," should be inserted before --tetrahydrobenzocycloheptenyl--.

Signed and Sealed this

Fourth Day of December, 1990

Attest:

HARRY F. MANBECK, JR.

Attesting Officer     Commissioner of Patents and Trademarks

UNITED STATES PATENT AND TRADEMARK OFFICE
CERTIFICATE OF CORRECTION

PATENT NO. : 4,880,809

DATED : November 14, 1989

INVENTOR(S) : Hirosada SUGIHARA et al.

It is certified that error appears in the above-identified patent and that said Letters Patent is hereby corrected as shown below:

Column 57, line 20, "acenaphythylenyl" should be corrected to read --acenaphthylenyl--.

Signed and Sealed this

Thirty-first Day of August, 1993

*Attest:*

BRUCE LEHMAN

*Attesting Officer*     *Commissioner of Patents and Trademarks*